(12) United States Patent
Xu

(10) Patent No.: US 11,168,149 B2
(45) Date of Patent: Nov. 9, 2021

(54) HETERODIMER MOLECULE BASED ON CH3 DOMAIN, AND PREPARATION METHOD AND USE THEREOF

(71) Applicants: JIANGSU ALPHAMAB BIOPHARMACEUTICALS CO., LTD., Jiangsu (CN); SUZHOU ALPHAMAB CO., LTD., Jiangsu (CN)

(72) Inventor: Ting Xu, Jiangsu (CN)

(73) Assignees: JIANGSU ALPHAMAB BIOPHARMACEUTICALS CO., LTD., Jiangsu (CN); SUZHOU ALPHAMAB CO., LTD., Jiangsu (CN)

( * ) Notice: Subject to any disclaimer, the term of this patent is extended or adjusted under 35 U.S.C. 154(b) by 131 days.

(21) Appl. No.: 16/062,405

(22) PCT Filed: Dec. 16, 2016

(86) PCT No.: PCT/CN2016/110252
§ 371 (c)(1),
(2) Date: Jun. 14, 2018

(87) PCT Pub. No.: WO2017/101828
PCT Pub. Date: Jun. 22, 2017

(65) Prior Publication Data
US 2018/0362668 A1 Dec. 20, 2018

(30) Foreign Application Priority Data
Dec. 16, 2015 (CN) .......................... 201510938995.0

(51) Int. Cl.
| | |
|---|---|
| *C07K 16/46* | (2006.01) |
| *C12P 21/00* | (2006.01) |
| *C12N 15/11* | (2006.01) |
| *A61K 39/395* | (2006.01) |
| *C07K 16/00* | (2006.01) |
| *C07K 19/00* | (2006.01) |
| *C12N 15/62* | (2006.01) |

(52) U.S. Cl.
CPC .......... *C07K 16/468* (2013.01); *A61K 39/395* (2013.01); *C07K 16/00* (2013.01); *C07K 16/46* (2013.01); *C07K 19/00* (2013.01); *C12N 15/11* (2013.01); *C12N 15/62* (2013.01); *C12P 21/00* (2013.01); *C07K 2317/31* (2013.01); *C07K 2317/524* (2013.01); *C07K 2317/526* (2013.01); *C07K 2317/94* (2013.01); *C07K 2319/74* (2013.01)

(58) Field of Classification Search
CPC .................................................. C07K 2317/526
USPC ...................................................... 424/136.1
See application file for complete search history.

(56) References Cited

U.S. PATENT DOCUMENTS

| | | | |
|---|---|---|---|
| 9,562,109 B2* | 2/2017 | Von Kreudenstein | ....................... C07K 16/32 |
| 9,574,010 B2* | 2/2017 | Spreter Von Kreudenstein | .......... C07K 16/46 |
| 9,951,145 B2* | 4/2018 | Kim | ....................... C07K 16/46 |
| 10,457,742 B2* | 10/2019 | Spreter Von Kreudenstein | .......... C07K 16/2887 |
| 2012/0149876 A1* | 6/2012 | Von Kreudenstein | ....................... C07K 16/32 530/387.3 |
| 2013/0195849 A1* | 8/2013 | Spreter Von Kreudenstein | .......... G16B 5/00 424/133.1 |
| 2013/0336973 A1* | 12/2013 | Spreter Von Kreudenstein | .......... C07K 16/2863 424/134.1 |
| 2014/0072579 A1 | 3/2014 | De Kruif et al. | |
| 2016/0257763 A1* | 9/2016 | Von Kreudenstein | ....................... C07K 16/2863 |
| 2018/0016347 A1* | 1/2018 | SpreterVon Kreudenstein | ........... G16B 5/00 |
| 2018/0194860 A1* | 7/2018 | Von Kreudenstein | ....................... C07K 16/468 |
| 2020/0087414 A1* | 3/2020 | SpreterVon Kreudenstein | ........... C07K 16/46 |
| 2020/0268902 A1* | 8/2020 | Xu | ......................... A61K 45/06 |
| 2020/0277350 A1* | 9/2020 | Xu | ......................... C07K 16/32 |
| 2020/0354478 A1* | 11/2020 | Xu | ...................... C07K 16/2863 |
| 2021/0162061 A1* | 6/2021 | Xu | ........................ A61K 31/704 |

FOREIGN PATENT DOCUMENTS

| | | |
|---|---|---|
| CN | 102558355 A | 7/2012 |
| CN | 102851338 A | 1/2013 |
| JP | 2015-515275 A | 5/2015 |
| WO | WO 2009/089004 A1 | 7/2009 |
| WO | WO 2011/090761 A1 | 7/2011 |
| WO | WO 2012/131555 A2 | 10/2012 |
| WO | WO2013097430 * | 4/2013 |

(Continued)

OTHER PUBLICATIONS

Wei et al. (Oncotarget, 2017, vol. 8, (No. 31), p. 51037-51049).*

(Continued)

*Primary Examiner* — Lynn A Bristol
(74) *Attorney, Agent, or Firm* — Scully, Scott, Murphy & Presser, P.C.

(57) ABSTRACT

The disclosure is directed to a heterodimer molecule, comprising a first polypeptide chain and a second polypeptide chain, and the first polypeptide chain comprises a first CH3 domain of an antibody heavy chain constant region, the second polypeptide chain comprises a second CH3 domain of an antibody heavy chain constant region. Comparing to a corresponding wild-type CH3 domain of a human antibody heavy chain constant region, the first CH3 domain and the second CH3 domain comprise amino acid mutations at specific positions, for example T366+K409+K392 and T366+L368+Y407+D399+F405, respectively.

8 Claims, 2 Drawing Sheets

Specification includes a Sequence Listing.

(56) References Cited

FOREIGN PATENT DOCUMENTS

WO    WO 2014/012085 A2    1/2014

OTHER PUBLICATIONS

Elliott et al (J. Mol. Biol. (2014) 426, 1947-1957).*
Ha et al. (Frontiers in Immunology 7:394 (Oct. 6, 2016)).*
Ridgeway et al. (Protein Engineering 9(7):617-621 (1996)).*
Atwell S. et al., "Stable Heterodimers for Remodeling the Domain Interface of a Homodimer Using a Phage Display Library", J. Mol. Biol. 270(1):26-35 (Jul. 4, 1997).
Merchant A.M. et al., "An Efficient Route to Human Bispecific IgG", Nature Biotechnology 16(7):677-681 (Jul. 1, 1998).
Partial Supplementary European Search Report dated May 23, 2019 received in European Application No. 16 87 4885.3.
International Search Report dated Feb. 9, 2017 issued in PCT/CN2016/110252.

* cited by examiner

SEQUENCE LISTING

<160> NUMBER OF SEQ ID NOS: 36

<210> SEQ ID NO 1
<211> LENGTH: 227
<212> TYPE: PRT
<213> ORGANISM: Homo sapiens

<400> SEQUENCE: 1

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225
```

<210> SEQ ID NO 2
<211> LENGTH: 681
<212> TYPE: DNA
<213> ORGANISM: Homo sapiens

<400> SEQUENCE: 2

```
gacaagaccc acacctgccc ccctgcccc  gccccgagc  tgctgggcgg ccccagcgtg    60
ttcctgttcc ccccaagcc  caaggacacc ctgatgatca gccgcacccc cgaggtgacc   120
tgcgtggtgg tggacgtgag ccacgagaac cccgaggtga agttcaactg gtacgtggac   180
ggcgtggagg tgcacaacgc caagaccaag ccccgcgagg agcagtacaa cagcacctac   240
cgcgtggtga gcgtgctgac cgtgctgcac caggactggc tgaacggcaa ggagtacaag   300
tgcaaggtga gcaacaaggc cctgcccgcc ccatcgaga  agaccatcag caaggccaag   360
ggccagcccc gcgagcccca ggtgtacacc ctgcccccca gccgcgacga gctgaccaag   420
aaccaggtga gcctgacctg cctggtgaag ggcttctacc ccagcgacat cgccgtggag   480
tgggagagca acggccagcc cgagaacaac tacaagacca ccccccccgt gctggacagc   540
gacggcagct tcttcctgta cagcaagctg accgtggaca gagccgctg  gcagcagggc   600
aacgtgttca gctgcagcgt gatgcacgag gccctgcaca accactacac ccagaagagc   660
ctgagcctga gccccggcaa g                                             681
```

<210> SEQ ID NO 3
<211> LENGTH: 741
<212> TYPE: DNA
<213> ORGANISM: artificial sequence
<220> FEATURE:
<223> OTHER INFORMATION: kappaIII signal peptide

<400> SEQUENCE: 3

```
atggagaccg acaccctgct gctgtgggtg ctgctgctgt gggtgcccgg cagcaccggc    60
gacaagaccc acacctgccc ccctgcccc gccccgagc tgctgggcgg ccccagcgtg   120
ttcctgttcc cccccaagcc caaggacacc ctgatgatca gccgcacccc cgaggtgacc   180
tgcgtggtgg tggacgtgag ccacgagaac cccgaggtga agttcaactg gtacgtggac   240
ggcgtggagg tgcacaacgc caagaccaag ccccgcgagg agcagtacaa cagcacctac   300
cgcgtggtga gcgtgctgac cgtgctgcac caggactggc tgaacggcaa ggagtacaag   360
tgcaaggtga gcaacaaggc cctgcccgcc cccatcgaga agaccatcag caaggccaag   420
ggccagcccc gcgagcccca ggtgtacacc ctgccccca gccgcgacga gctgaccaag   480
aaccaggtga gcctgacctg cctggtgaag ggcttctacc ccagcgacat cgccgtggag   540
tgggagagca acggccagcc cgagaacaac tacaagacca ccccccccgt gctggacagc   600
gacggcagct tcttcctgta cagcaagctg accgtggaca gagccgctg cagcagggc    660
aacgtgttca gctgcagcgt gatgcacgag gccctgcaca accactacac ccagaagagc   720
ctgagcctga gccccggcaa g                                            741
```

<210> SEQ ID NO 4
<211> LENGTH: 471
<212> TYPE: PRT
<213> ORGANISM: artificial sequence
<220> FEATURE:
<223> OTHER INFORMATION: a ScFv-Fc fusion protein

<400> SEQUENCE: 4

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Gly Ser Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175
```

Gly Gln Ala Pro Arg Leu Leu Ile Tyr Ala Ala Ser Thr Arg Ala Thr
                180                 185                 190

Gly Ile Pro Ala Arg Phe Ser Gly Ser Gly Ser Gly Thr Glu Phe Thr
            195                 200                 205

Leu Thr Ile Ser Ser Leu Gln Ser Glu Asp Phe Ala Val Tyr Tyr Cys
        210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 5
<211> LENGTH: 1473
<212> TYPE: DNA
<213> ORGANISM: artificial sequence
<220> FEATURE:
<223> OTHER INFORMATION: ScFv-Fc fusion protein coding gene

<400> SEQUENCE: 5
atggagaccg acaccctgct gctgtgggtg ctgctgctgt gggtgcccgg cagcaccggc     60
gaggtgcagc tgctggagag cggcggcggc gtggtgcagc ccggccgcag cctgcgcctg    120
agctgcatcg ccagcggctt caccttcagc agctaccccc tgacctgggt cgcgcaggcc    180
cccggcaagg gcctggagtg ggtggccagc atcagctacg acggcagcta caagtacaag    240
gccgacagca tgaagggccg cctgaccatc agccgcgaca acagcaagaa cacccctgtac   300 ctggagatga acagcctgac cgccgaggac accgccgtgt actactgcgc ccgcaccgcc    360

-continued

```
ttcttcaacg cctacgactt ctggggccag ggcaccctgg tgaccgtgag cagcgccagc    420
accaagggcc ccagcgtggg cggcggcggc agcggcggcg gcggcagcga gatcgtgatg    480
acccagagcc ccgccaccct gagcgtgagc cccggcgagc gcgccaccct gagctgccgc    540
gccagccaga gcgtgcgcag caacctggcc tggtaccagc agaagcccgg ccaggccccc    600
cgcctgctga tctacgccgc cagcacccgc gccaccggca tccccgcccg cttcagcggc    660
agcggcagcg gcaccgagtt caccctgacc atcagcagcc tgcagagcga ggacttcgcc    720
gtgtactact gccagcagta caacgagtgg ttccgcacca gcggccaggg caccaaggtg    780
gagatcaagc gcgacaagac ccacacctgc cccccctgcc ccgcccccga gctgctgggc    840
ggccccagcg tgttcctgtt ccccccaag cccaaggaca ccctgatgat cagccgcacc    900
cccgaggtga cctgcgtggt ggtggacgtg agccacgaga cccccgaggt gaagttcaac    960
tggtacgtgg acggcgtgga ggtgcacaac gccaagacca gccccgcga ggagcagtac    1020 aacagcacct accgcgtggt gagcgtgctg accgtgctgc accaggactg gctgaacggc    1080
aaggagtaca agtgcaaggt gagcaacaag gccctgcccg cccccatcga aagaccatc    1140 agcaaggcca agggccagcc ccgcgagccc caggtgtaca ccctgccccc cagccgcgac    1200
gagctgacca gaaccaggt gagcctgacc tgcctggtga agggcttcta ccccagcgac    1260
atcgccgtgg agtgggagag caacggccag cccgagaaca actacaagac ccccccccc    1320 gtgctggaca gcgacggcag cttcttcctg tacagcaagc tgaccgtgga caagagccgc    1380
tggcagcagg gcaacgtgtt cagctgcagc gtgatgcacg aggccctgca caaccactac    1440
acccagaaga gcctgagcct gagccccggc aag                                 1473
```

<210> SEQ ID NO 6
<211> LENGTH: 471
<212> TYPE: PRT
<213> ORGANISM: artificial sequence
<220> FEATURE:
<223> OTHER INFORMATION: Y349C+T366W

<400> SEQUENCE: 6

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Gly Ser Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
```

```
                    165                 170                 175
Gly Gln Ala Pro Arg Leu Leu Ile Tyr Ala Ala Ser Thr Arg Ala Thr
                180                 185                 190
Gly Ile Pro Ala Arg Phe Ser Gly Ser Gly Ser Gly Thr Glu Phe Thr
            195                 200                 205
Leu Thr Ile Ser Ser Leu Gln Ser Glu Asp Phe Ala Val Tyr Tyr Cys
        210                 215                 220
Gln Gln Tyr Asn Glu Trp Phe Arg Thr Ser Gly Gln Gly Thr Lys Val
225                 230                 235                 240
Glu Ile Lys Arg Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asn Pro Glu Val Lys Phe Asn Trp Tyr Val Asp
        290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
            355                 360                 365
Glu Pro Gln Val Cys Thr Leu Pro Pro Ser Arg Asp Glu Leu Thr Lys
        370                 375                 380
Asn Gln Val Ser Leu Trp Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 7
<211> LENGTH: 227
<212> TYPE: PRT
<213> ORGANISM: artificial sequence
<220> FEATURE:
<223> OTHER INFORMATION: D356C+T366S+L368A+Y407V

<400> SEQUENCE: 7

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
```

```
                50                  55                  60
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 227
<212> TYPE: PRT
<213> ORGANISM: artificial sequence
<220> FEATURE:
<223> OTHER INFORMATION: D356C+T366S+L368A+Y407V+F405K

<400> SEQUENCE: 8

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
```

-continued

```
                180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
        210                 215                 220
Pro Gly Lys
225

<210> SEQ ID NO 9
<211> LENGTH: 471
<212> TYPE: PRT
<213> ORGANISM: artificial sequence
<220> FEATURE:
<223> OTHER INFORMATION: Y349C+T366W+F405K

<400> SEQUENCE: 9

Glu Val Gln Leu Leu Glu Ser Gly Gly Gly Val Val Gln Pro Gly Arg
1               5                   10                  15
Ser Leu Arg Leu Ser Cys Ile Ala Ser Gly Phe Thr Phe Ser Ser Tyr
            20                  25                  30
Pro Met Thr Trp Val Arg Gln Ala Pro Gly Lys Gly Leu Glu Trp Val
        35                  40                  45
Ala Ser Ile Ser Tyr Asp Gly Ser Tyr Lys Tyr Lys Ala Asp Ser Met
    50                  55                  60
Lys Gly Arg Leu Thr Ile Ser Arg Asp Asn Ser Lys Asn Thr Leu Tyr
65                  70                  75                  80
Leu Glu Met Asn Ser Leu Thr Ala Glu Asp Thr Ala Val Tyr Tyr Cys
                85                  90                  95
Ala Arg Thr Ala Phe Phe Asn Ala Tyr Asp Phe Trp Gly Gln Gly Thr
            100                 105                 110
Leu Val Thr Val Ser Ser Ala Ser Thr Lys Gly Pro Ser Val Gly Gly
        115                 120                 125
Gly Gly Ser Gly Gly Gly Ser Glu Ile Val Met Thr Gln Ser Pro
    130                 135                 140
Ala Thr Leu Ser Val Ser Pro Gly Glu Arg Ala Thr Leu Ser Cys Arg
145                 150                 155                 160
Ala Ser Gln Ser Val Arg Ser Asn Leu Ala Trp Tyr Gln Gln Lys Pro
                165                 170                 175
Gly Gln Ala Pro Arg Leu Leu Ile Tyr Ala Ala Ser Thr Arg Ala Thr
            180                 185                 190
Gly Ile Pro Ala Arg Phe Ser Gly Ser Gly Ser Gly Thr Glu Phe Thr
        195                 200                 205
Leu Thr Ile Ser Ser Leu Gln Ser Glu Asp Phe Ala Val Tyr Tyr Cys
    210                 215                 220
Gln Gln Tyr Asn Glu Trp Phe Arg Thr Ser Gly Gln Gly Thr Lys Val
225                 230                 235                 240
Glu Ile Lys Arg Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asn Pro Glu Val Lys Phe Asn Trp Tyr Val Asp
    290                 295                 300
Gly Val Glu Val His Asn Ala Lys Thr Lys Pro Arg Glu Glu Gln Tyr
```

```
             305                 310                 315                 320
Asn Ser Thr Tyr Arg Val Val Ser Val Leu Thr Val Leu His Gln Asp
                    325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
            355                 360                 365
Glu Pro Gln Val Cys Thr Leu Pro Pro Ser Arg Asp Glu Leu Thr Lys
        370                 375                 380
Asn Gln Val Ser Leu Trp Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Lys Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 10
<211> LENGTH: 471
<212> TYPE: PRT
<213> ORGANISM: artificial sequence
<220> FEATURE:
<223> OTHER INFORMATION: Y349C+T366W+K409E

<400> SEQUENCE: 10

Glu Val Gln Leu Leu Glu Ser Gly Gly Gly Val Val Gln Pro Gly Arg
1               5                   10                  15
Ser Leu Arg Leu Ser Cys Ile Ala Ser Gly Phe Thr Phe Ser Ser Tyr
            20                  25                  30
Pro Met Thr Trp Val Arg Gln Ala Pro Gly Lys Gly Leu Glu Trp Val
        35                  40                  45
Ala Ser Ile Ser Tyr Asp Gly Ser Tyr Lys Tyr Lys Ala Asp Ser Met
    50                  55                  60
Lys Gly Arg Leu Thr Ile Ser Arg Asp Asn Ser Lys Asn Thr Leu Tyr
65                  70                  75                  80
Leu Glu Met Asn Ser Leu Thr Ala Glu Asp Thr Ala Val Tyr Tyr Cys
                85                  90                  95
Ala Arg Thr Ala Phe Phe Asn Ala Tyr Asp Phe Trp Gly Gln Gly Thr
            100                 105                 110
Leu Val Thr Val Ser Ser Ala Ser Thr Lys Gly Pro Ser Val Gly Gly
        115                 120                 125
Gly Gly Ser Gly Gly Gly Ser Glu Ile Val Met Thr Gln Ser Pro
    130                 135                 140
Ala Thr Leu Ser Val Ser Pro Gly Glu Arg Ala Thr Leu Ser Cys Arg
145                 150                 155                 160
Ala Ser Gln Ser Val Arg Ser Asn Leu Ala Trp Tyr Gln Gln Lys Pro
                165                 170                 175
Gly Gln Ala Pro Arg Leu Leu Ile Tyr Ala Ala Ser Thr Arg Ala Thr
            180                 185                 190
Gly Ile Pro Ala Arg Phe Ser Gly Ser Gly Ser Gly Thr Glu Phe Thr
```

```
                195                 200                 205
Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Cys Thr Leu Pro Pro Ser Arg Asp Glu Leu Thr Lys
    370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Glu Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 11
<211> LENGTH: 471
<212> TYPE: PRT
<213> ORGANISM: artificial sequence
<220> FEATURE:
<223> OTHER INFORMATION: Y349C+T366W+K409A

<400> SEQUENCE: 11

Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
                20                  25                  30

Pro Met Thr Trp Val Arg Gln Ala Pro Gly Lys Gly Leu Glu Trp Val
            35                  40                  45

Ala Ser Ile Ser Tyr Asp Gly Ser Tyr Lys Tyr Lys Ala Asp Ser Met
        50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
```

```
                    85                  90                  95
Ala Arg Thr Ala Phe Asn Ala Tyr Asp Phe Trp Gln Gly Thr
                100                 105                 110

Leu Val Thr Val Ser Ser Ala Ser Thr Lys Gly Pro Ser Val Gly Gly
            115                 120                 125

Gly Gly Ser Gly Gly Gly Ser Glu Ile Val Met Thr Gln Ser Pro
        130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
                180                 185                 190

Gly Ile Pro Ala Arg Phe Ser Gly Ser Gly Ser Gly Thr Glu Phe Thr
                195                 200                 205

Leu Thr Ile Ser Ser Leu Gln Ser Glu Asp Phe Ala Val Tyr Tyr Cys
            210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asn Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Cys Thr Leu Pro Pro Ser Arg Asp Glu Leu Thr Lys
            370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Ala Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 12
<211> LENGTH: 471
<212> TYPE: PRT
<213> ORGANISM: artificial sequence
```

<220> FEATURE:
<223> OTHER INFORMATION: Y349C+T366W+F405K+K360E+Q347E

<400> SEQUENCE: 12

| | | | | | | | | | | | | | |
|---|---|---|---|---|---|---|---|---|---|---|---|---|---|
| Glu | Val | Gln | Leu | Leu | Glu | Ser | Gly | Gly | Gly | Val | Val | Gln | Pro | Gly | Arg |
| 1 | | | | 5 | | | | | 10 | | | | | 15 | |

| Ser | Leu | Arg | Leu | Ser | Cys | Ile | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Pro | Met | Thr | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Ser | Ile | Ser | Tyr | Asp | Gly | Ser | Tyr | Lys | Tyr | Lys | Ala | Asp | Ser | Met |
|---|---|---|---|---|---|---|---|---|---|---|---|---|---|---|---|
| 50 | | | | | 55 | | | | | 60 | | | | | |

| Lys | Gly | Arg | Leu | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Glu | Met | Asn | Ser | Leu | Thr | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Thr | Ala | Phe | Phe | Asn | Ala | Tyr | Asp | Phe | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser | Ala | Ser | Thr | Lys | Gly | Pro | Ser | Val | Gly | Gly |
|---|---|---|---|---|---|---|---|---|---|---|---|---|---|---|---|
| | | 115 | | | | | 120 | | | | | 125 | | | |

| Gly | Gly | Ser | Gly | Gly | Gly | Ser | Glu | Ile | Val | Met | Thr | Gln | Ser | Pro |
|---|---|---|---|---|---|---|---|---|---|---|---|---|---|---|
| | 130 | | | | | 135 | | | | | 140 | | | |

| Ala | Thr | Leu | Ser | Val | Ser | Pro | Gly | Glu | Arg | Ala | Thr | Leu | Ser | Cys | Arg |
|---|---|---|---|---|---|---|---|---|---|---|---|---|---|---|---|
| 145 | | | | | 150 | | | | | 155 | | | | | 160 |

| Ala | Ser | Gln | Ser | Val | Arg | Ser | Asn | Leu | Ala | Trp | Tyr | Gln | Gln | Lys | Pro |
|---|---|---|---|---|---|---|---|---|---|---|---|---|---|---|---|
| | | | | 165 | | | | | 170 | | | | | 175 | |

| Gly | Gln | Ala | Pro | Arg | Leu | Leu | Ile | Tyr | Ala | Ala | Ser | Thr | Arg | Ala | Thr |
|---|---|---|---|---|---|---|---|---|---|---|---|---|---|---|---|
| | | | 180 | | | | | 185 | | | | | 190 | | |

| Gly | Ile | Pro | Ala | Arg | Phe | Ser | Gly | Ser | Gly | Ser | Gly | Thr | Glu | Phe | Thr |
|---|---|---|---|---|---|---|---|---|---|---|---|---|---|---|---|
| | | | 195 | | | | | 200 | | | | | 205 | | |

| Leu | Thr | Ile | Ser | Ser | Leu | Gln | Ser | Glu | Asp | Phe | Ala | Val | Tyr | Tyr | Cys |
|---|---|---|---|---|---|---|---|---|---|---|---|---|---|---|---|
| | 210 | | | | | 215 | | | | | 220 | | | | |

| Gln | Gln | Tyr | Asn | Glu | Trp | Phe | Arg | Thr | Ser | Gly | Gln | Gly | Thr | Lys | Val |
|---|---|---|---|---|---|---|---|---|---|---|---|---|---|---|---|
| 225 | | | | | 230 | | | | | 235 | | | | | 240 |

| Glu | Ile | Lys | Arg | Asp | Lys | Thr | His | Thr | Cys | Pro | Pro | Cys | Pro | Ala | Pro |
|---|---|---|---|---|---|---|---|---|---|---|---|---|---|---|---|
| | | | | 245 | | | | | 250 | | | | | 255 | |

| Glu | Leu | Leu | Gly | Gly | Pro | Ser | Val | Phe | Leu | Phe | Pro | Pro | Lys | Pro | Lys |
|---|---|---|---|---|---|---|---|---|---|---|---|---|---|---|---|
| | | | 260 | | | | | 265 | | | | | 270 | | |

| Asp | Thr | Leu | Met | Ile | Ser | Arg | Thr | Pro | Glu | Val | Thr | Cys | Val | Val | Val |
|---|---|---|---|---|---|---|---|---|---|---|---|---|---|---|---|
| | | 275 | | | | | 280 | | | | | 285 | | | |

| Asp | Val | Ser | His | Glu | Asn | Pro | Glu | Val | Lys | Phe | Asn | Trp | Tyr | Val | Asp |
|---|---|---|---|---|---|---|---|---|---|---|---|---|---|---|---|
| | 290 | | | | | 295 | | | | | 300 | | | | |

| Gly | Val | Glu | Val | His | Asn | Ala | Lys | Thr | Lys | Pro | Arg | Glu | Glu | Gln | Tyr |
|---|---|---|---|---|---|---|---|---|---|---|---|---|---|---|---|
| 305 | | | | | 310 | | | | | 315 | | | | | 320 |

| Asn | Ser | Thr | Tyr | Arg | Val | Val | Ser | Val | Leu | Thr | Val | Leu | His | Gln | Asp |
|---|---|---|---|---|---|---|---|---|---|---|---|---|---|---|---|
| | | | | 325 | | | | | 330 | | | | | 335 | |

| Trp | Leu | Asn | Gly | Lys | Glu | Tyr | Lys | Cys | Lys | Val | Ser | Asn | Lys | Ala | Leu |
|---|---|---|---|---|---|---|---|---|---|---|---|---|---|---|---|
| | | | 340 | | | | | 345 | | | | | 350 | | |

| Pro | Ala | Pro | Ile | Glu | Lys | Thr | Ile | Ser | Lys | Ala | Lys | Gly | Gln | Pro | Arg |
|---|---|---|---|---|---|---|---|---|---|---|---|---|---|---|---|
| | | 355 | | | | | 360 | | | | | 365 | | | |

| Glu | Pro | Glu | Val | Cys | Thr | Leu | Pro | Pro | Ser | Arg | Asp | Glu | Leu | Thr | Glu |
|---|---|---|---|---|---|---|---|---|---|---|---|---|---|---|---|
| | 370 | | | | | 375 | | | | | 380 | | | | |

| Asn | Gln | Val | Ser | Leu | Trp | Cys | Leu | Val | Lys | Gly | Phe | Tyr | Pro | Ser | Asp |
|---|---|---|---|---|---|---|---|---|---|---|---|---|---|---|---|
| 385 | | | | | 390 | | | | | 395 | | | | | 400 |

```
Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Lys Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465             470
```

```
<210> SEQ ID NO 13
<211> LENGTH: 227
<212> TYPE: PRT
<213> ORGANISM: artificial sequence
<220> FEATURE:
<223> OTHER INFORMATION: D356C+T366S+L368A+Y407V+Q347R

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

```
<210> SEQ ID NO 14
<211> LENGTH: 471
<212> TYPE: PRT
<213> ORGANISM: artificial sequence
<220> FEATURE:
<223> OTHER INFORMATION: Y349C+T366W+F405K+Q347R
```

<400> SEQUENCE: 14

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Ser Glu Ile Val Met Thr Gln Ser Pro
130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Arg Val Cys Thr Leu Pro Pro Ser Arg Asp Glu Leu Thr Lys
    370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

Thr Thr Pro Pro Val Leu Asp Ser Asp Gly Ser Phe Lys Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465             470

<210> SEQ ID NO 15
<211> LENGTH: 227
<212> TYPE: PRT
<213> ORGANISM: artificial sequence
<220> FEATURE:
<223> OTHER INFORMATION: D356C+T366S+L368A+Y407V+K360E+Q347E

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 16
<211> LENGTH: 471
<212> TYPE: PRT
<213> ORGANISM: artificial sequence
<220> FEATURE:
<223> OTHER INFORMATION: Y349C+T366W+K409A+K360E+Q347E

<400> SEQUENCE: 16

Glu Val Gln Leu Leu Glu Ser Gly Gly Gly Val Val Gln Pro Gly Arg

-continued

```
1               5                   10                  15
Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
            35                  40                  45

Ala Ser Ile Ser Tyr Asp Gly Ser Tyr Lys Tyr Ala Asp Ser Met
            50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
                100                 105                 110

Leu Val Thr Val Ser Ser Ala Ser Thr Lys Gly Pro Ser Val Gly Gly
                115                 120                 125

Gly Gly Ser Gly Gly Gly Ser Glu Ile Val Met Thr Gln Ser Pro
            130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
                180                 185                 190

Gly Ile Pro Ala Arg Phe Ser Gly Ser Gly Ser Gly Thr Glu Phe Thr
                195                 200                 205

Leu Thr Ile Ser Ser Leu Gln Ser Glu Asp Phe Ala Val Tyr Tyr Cys
210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asn Pro Glu Val Lys Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Glu Val Cys Thr Leu Pro Pro Ser Arg Asp Glu Leu Thr Glu
                370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430
```

Ala Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465             470

<210> SEQ ID NO 17
<211> LENGTH: 227
<212> TYPE: PRT
<213> ORGANISM: artificial sequence
<220> FEATURE:
<223> OTHER INFORMATION: D356C+T366S+L368A+Y407V+F405K+Q347R

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 18
<211> LENGTH: 471
<212> TYPE: PRT
<213> ORGANISM: artificial sequence
<220> FEATURE:
<223> OTHER INFORMATION: Y349C+T366W+K409A+Q347R

<400> SEQUENCE: 18

Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr

```
                20                  25                  30
Pro Met Thr Trp Val Arg Gln Ala Pro Gly Lys Gly Leu Glu Trp Val
            35                  40                  45
Ala Ser Ile Ser Tyr Asp Gly Ser Tyr Lys Tyr Lys Ala Asp Ser Met
        50                  55                  60
Lys Gly Arg Leu Thr Ile Ser Arg Asp Asn Ser Lys Asn Thr Leu Tyr
65                  70                  75                  80
Leu Glu Met Asn Ser Leu Thr Ala Glu Asp Thr Ala Val Tyr Tyr Cys
                85                  90                  95
Ala Arg Thr Ala Phe Phe Asn Ala Tyr Asp Phe Trp Gly Gln Gly Thr
            100                 105                 110
Leu Val Thr Val Ser Ser Ala Ser Thr Lys Gly Pro Ser Val Gly Gly
            115                 120                 125
Gly Gly Ser Gly Gly Gly Ser Glu Ile Val Met Thr Gln Ser Pro
        130                 135                 140
Ala Thr Leu Ser Val Ser Pro Gly Glu Arg Ala Thr Leu Ser Cys Arg
145                 150                 155                 160
Ala Ser Gln Ser Val Arg Ser Asn Leu Ala Trp Tyr Gln Gln Lys Pro
                165                 170                 175
Gly Gln Ala Pro Arg Leu Leu Ile Tyr Ala Ala Ser Thr Arg Ala Thr
            180                 185                 190
Gly Ile Pro Ala Arg Phe Ser Gly Ser Gly Ser Gly Thr Glu Phe Thr
        195                 200                 205
Leu Thr Ile Ser Ser Leu Gln Ser Glu Asp Phe Ala Val Tyr Tyr Cys
            210                 215                 220
Gln Gln Tyr Asn Glu Trp Phe Arg Thr Ser Gly Gln Gly Thr Lys Val
225                 230                 235                 240
Glu Ile Lys Arg Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asn Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Arg Val Cys Thr Leu Pro Pro Ser Arg Asp Glu Leu Thr Lys
    370                 375                 380
Asn Gln Val Ser Leu Trp Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Ala Leu Thr Val Asp Lys Ser Arg Trp Gln Gln Gly Asn Val Phe Ser
        435                 440                 445
```

<210> SEQ ID NO 19
<211> LENGTH: 227
<212> TYPE: PRT
<213> ORGANISM: artificial sequence
<220> FEATURE:
<223> OTHER INFORMATION: D356C+T366S+L368A+Y407V+F405K+K360E+Q347E

<400> SEQUENCE: 19

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 20
<211> LENGTH: 471
<212> TYPE: PRT
<213> ORGANISM: artificial sequence
<220> FEATURE:
<223> OTHER INFORMATION: Y349C+T366W+K409A+L368E

<400> SEQUENCE: 20

Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val

```
                35                  40                  45
Ala Ser Ile Ser Tyr Asp Gly Ser Tyr Lys Tyr Lys Ala Asp Ser Met
     50                  55                  60
Lys Gly Arg Leu Thr Ile Ser Arg Asp Asn Ser Lys Asn Thr Leu Tyr
 65                  70                  75                  80
Leu Glu Met Asn Ser Leu Thr Ala Glu Asp Thr Ala Val Tyr Tyr Cys
                 85                  90                  95
Ala Arg Thr Ala Phe Phe Asn Ala Tyr Asp Phe Trp Gly Gln Gly Thr
                100                 105                 110
Leu Val Thr Val Ser Ser Ala Ser Thr Lys Gly Pro Ser Val Gly Gly
                115                 120                 125
Gly Gly Ser Gly Gly Gly Ser Glu Ile Val Met Thr Gln Ser Pro
    130                 135                 140
Ala Thr Leu Ser Val Ser Pro Gly Glu Arg Ala Thr Leu Ser Cys Arg
145                 150                 155                 160
Ala Ser Gln Ser Val Arg Ser Asn Leu Ala Trp Tyr Gln Gln Lys Pro
                165                 170                 175
Gly Gln Ala Pro Arg Leu Leu Ile Tyr Ala Ala Ser Thr Arg Ala Thr
                180                 185                 190
Gly Ile Pro Ala Arg Phe Ser Gly Ser Gly Ser Gly Thr Glu Phe Thr
                195                 200                 205
Leu Thr Ile Ser Ser Leu Gln Ser Glu Asp Phe Ala Val Tyr Tyr Cys
    210                 215                 220
Gln Gln Tyr Asn Glu Trp Phe Arg Thr Ser Gly Gln Gly Thr Lys Val
225                 230                 235                 240
Glu Ile Lys Arg Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
    275                 280                 285
Asp Val Ser His Glu Asn Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
                355                 360                 365
Glu Pro Gln Val Cys Thr Leu Pro Pro Ser Arg Asp Glu Leu Thr Lys
                370                 375                 380
Asn Gln Val Ser Leu Trp Cys Glu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
                420                 425                 430
Ala Leu Thr Val Asp Lys Ser Arg Trp Gln Gln Gly Asn Val Phe Ser
                435                 440                 445
Cys Ser Val Met His Glu Ala Leu His Asn His Tyr Thr Gln Lys Ser
                450                 455                 460
```

-continued

Leu Ser Leu Ser Pro Gly Lys
465                 470

<210> SEQ ID NO 21
<211> LENGTH: 471
<212> TYPE: PRT
<213> ORGANISM: artificial sequence
<220> FEATURE:
<223> OTHER INFORMATION: T366W+K409A+K392D

<400> SEQUENCE: 21

Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Ser Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

```
Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Asp
                405                 410                 415

Thr Thr Pro Pro Val Leu Asp Ser Asp Gly Ser Phe Phe Leu Tyr Ser
            420                 425                 430

Ala Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 22
<211> LENGTH: 227
<212> TYPE: PRT
<213> ORGANISM: artificial sequence
<220> FEATURE:
<223> OTHER INFORMATION: T366S+L368A+Y407V+D399S+F405K

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Ser Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225
```

<210> SEQ ID NO 23
<211> LENGTH: 471
<212> TYPE: PRT
<213> ORGANISM: artificial sequence
<220> FEATURE:
<223> OTHER INFORMATION: T366W+K409A

<400> SEQUENCE: 23

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Gly Ser Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365
```

Glu Pro Gln Val Tyr Thr Leu Pro Pro Ser Arg Asp Glu Leu Thr Lys
    370                 375                 380
Asn Gln Val Ser Leu Trp Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Ala Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 24
<211> LENGTH: 227
<212> TYPE: PRT
<213> ORGANISM: artificial sequence
<220> FEATURE:
<223> OTHER INFORMATION: T366S+L368G+Y407A+F405K

<400> SEQUENCE: 24

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Ser Cys Gly Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Lys Leu Ala Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 25

```
<211> LENGTH: 227
<212> TYPE: PRT
<213> ORGANISM: artificial sequence
<220> FEATURE:
<223> OTHER INFORMATION: T366S+L368A+Y407V+F405K+E357A

<400> SEQUENCE: 25
```

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Leu | Leu | Gly |
| 1 | | | | 5 | | | | | 10 | | | | | 15 | |
| Gly | Pro | Ser | Val | Phe | Leu | Phe | Pro | Pro | Lys | Pro | Lys | Asp | Thr | Leu | Met |
| | | | 20 | | | | | 25 | | | | | 30 | | |
| Ile | Ser | Arg | Thr | Pro | Glu | Val | Thr | Cys | Val | Val | Val | Asp | Val | Ser | His |
| | | | 35 | | | | | 40 | | | | | 45 | | |
| Glu | Asp | Pro | Glu | Val | Lys | Phe | Asn | Trp | Tyr | Val | Asp | Gly | Val | Glu | Val |
| | 50 | | | | | 55 | | | | | 60 | | | | |
| His | Asn | Ala | Lys | Thr | Lys | Pro | Arg | Glu | Glu | Gln | Tyr | Asn | Ser | Thr | Tyr |
| 65 | | | | | 70 | | | | | 75 | | | | | 80 |
| Arg | Val | Val | Ser | Val | Leu | Thr | Val | Leu | His | Gln | Asp | Trp | Leu | Asn | Gly |
| | | | | 85 | | | | | 90 | | | | | 95 | |
| Lys | Glu | Tyr | Lys | Cys | Lys | Val | Ser | Asn | Lys | Ala | Leu | Pro | Ala | Pro | Ile |
| | | | 100 | | | | | 105 | | | | | 110 | | |
| Glu | Lys | Thr | Ile | Ser | Lys | Ala | Lys | Gly | Gln | Pro | Arg | Glu | Pro | Gln | Val |
| | | | 115 | | | | | 120 | | | | | 125 | | |
| Tyr | Thr | Leu | Pro | Pro | Ser | Arg | Asp | Ala | Leu | Thr | Lys | Asn | Gln | Val | Ser |
| | 130 | | | | | 135 | | | | | 140 | | | | |
| Leu | Ser | Cys | Ala | Val | Lys | Gly | Phe | Tyr | Pro | Ser | Asp | Ile | Ala | Val | Glu |
| 145 | | | | | 150 | | | | | 155 | | | | | 160 |
| Trp | Glu | Ser | Asn | Gly | Gln | Pro | Glu | Asn | Asn | Tyr | Lys | Thr | Thr | Pro | Pro |
| | | | | 165 | | | | | 170 | | | | | 175 | |
| Val | Leu | Asp | Ser | Asp | Gly | Ser | Phe | Lys | Leu | Val | Ser | Lys | Leu | Thr | Val |
| | | | 180 | | | | | 185 | | | | | 190 | | |
| Asp | Lys | Ser | Arg | Trp | Gln | Gln | Gly | Asn | Val | Phe | Ser | Cys | Ser | Val | Met |
| | | | 195 | | | | | 200 | | | | | 205 | | |
| His | Glu | Ala | Leu | His | Asn | His | Tyr | Thr | Gln | Lys | Ser | Leu | Ser | Leu | Ser |
| | 210 | | | | | 215 | | | | | 220 | | | | |
| Pro | Gly | Lys | | | | | | | | | | | | | |
| 225 | | | | | | | | | | | | | | | |

```
<210> SEQ ID NO 26
<211> LENGTH: 471
<212> TYPE: PRT
<213> ORGANISM: artificial sequence
<220> FEATURE:
<223> OTHER INFORMATION: T366W+K409A+Y349D+S354D

<400> SEQUENCE: 26
```

| | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Ile | Ala | Ser | Gly | Phe | Thr | Phe | Ser | Ser | Tyr |
| | | | 20 | | | | | 25 | | | | | 30 | | |
| Pro | Met | Thr | Trp | Val | Arg | Gln | Ala | Pro | Gly | Lys | Gly | Leu | Glu | Trp | Val |
| | | | 35 | | | | | 40 | | | | | 45 | | |
| Ala | Ser | Ile | Ser | Tyr | Asp | Gly | Ser | Tyr | Lys | Tyr | Lys | Ala | Asp | Ser | Met |
| | 50 | | | | | 55 | | | | | 60 | | | | |
| Lys | Gly | Arg | Leu | Thr | Ile | Ser | Arg | Asp | Asn | Ser | Lys | Asn | Thr | Leu | Tyr |
| 65 | | | | | 70 | | | | | 75 | | | | | 80 |
| Leu | Glu | Met | Asn | Ser | Leu | Thr | Ala | Glu | Asp | Thr | Ala | Val | Tyr | Tyr | Cys |

```
                    85                  90                  95
Ala Arg Thr Ala Phe Asn Ala Tyr Asp Phe Trp Gly Gln Gly Thr
                100                 105                 110

Leu Val Thr Val Ser Ser Ala Ser Thr Lys Gly Pro Ser Val Gly
                115                 120                 125

Gly Gly Ser Gly Gly Gly Ser Glu Ile Val Met Thr Gln Ser Pro
130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
                180                 185                 190

Gly Ile Pro Ala Arg Phe Ser Gly Ser Gly Ser Gly Thr Glu Phe Thr
                195                 200                 205

Leu Thr Ile Ser Ser Leu Gln Ser Glu Asp Phe Ala Val Tyr Tyr Cys
                210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asn Pro Glu Val Lys Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Asp Thr Leu Pro Pro Asp Arg Asp Glu Leu Thr Lys
                370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Ala Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 27
<211> LENGTH: 471
<212> TYPE: PRT
<213> ORGANISM: artificial sequence
```

<220> FEATURE:
<223> OTHER INFORMATION: T366W+F405K

<400> SEQUENCE: 27

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Ser Glu Ile Val Met Thr Gln Ser Pro
130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Trp Cys Leu Val Lys Gly Phe Tyr Pro Ser Asp
385                 390                 395                 400
```

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Lys Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465             470

<210> SEQ ID NO 28
<211> LENGTH: 227
<212> TYPE: PRT
<213> ORGANISM: artificial sequence
<220> FEATURE:
<223> OTHER INFORMATION: T366S+L368A+Y407V+K409A

<400> SEQUENCE: 28

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 29
<211> LENGTH: 471
<212> TYPE: PRT
<213> ORGANISM: artificial sequence
<220> FEATURE:
<223> OTHER INFORMATION: T366W+F405K+D399S

```
<400> SEQUENCE: 29

Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Ser Glu Ile Val Met Thr Gln Ser Pro
130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

Thr Thr Pro Pro Val Leu Ser Ser Asp Gly Ser Phe Lys Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 30
<211> LENGTH: 227
<212> TYPE: PRT
<213> ORGANISM: artificial sequence
<220> FEATURE:
<223> OTHER INFORMATION: T366S+L368A+Y407V+K409A+K392D

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
            165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 31
<211> LENGTH: 227
<212> TYPE: PRT
<213> ORGANISM: artificial sequence
<220> FEATURE:
<223> OTHER INFORMATION: T366S+L368G+Y407A+K409A

<400> SEQUENCE: 31

Asp Lys Thr His Thr Cys Pro Pro Cys Pro Ala Pro Glu Leu Leu Gly

-continued

```
                1               5                      10                     15
            Gly Pro Ser Val Phe Leu Phe Pro Pro Lys Pro Lys Asp Thr Leu Met
                                20                     25                     30

Ile Ser Arg Thr Pro Glu Val Thr Cys Val Val Val Asp Val Ser His
                                35                     40                     45

Glu Asp Pro Glu Val Lys Phe Asn Trp Tyr Val Asp Gly Val Glu Val
                                50                     55                     60

His Asn Ala Lys Thr Lys Pro Arg Glu Glu Gln Tyr Asn Ser Thr Tyr
             65                     70                     75                     80

Arg Val Val Ser Val Leu Thr Val Leu His Gln Asp Trp Leu Asn Gly
                                85                     90                     95

Lys Glu Tyr Lys Cys Lys Val Ser Asn Lys Ala Leu Pro Ala Pro Ile
                               100                    105                    110

Glu Lys Thr Ile Ser Lys Ala Lys Gly Gln Pro Arg Glu Pro Gln Val
                               115                    120                    125

Tyr Thr Leu Pro Pro Ser Arg Asp Glu Leu Thr Lys Asn Gln Val Ser
                               130                    135                    140

Leu Ser Cys Gly Val Lys Gly Phe Tyr Pro Ser Asp Ile Ala Val Glu
            145                    150                    155                    160

Trp Glu Ser Asn Gly Gln Pro Glu Asn Asn Tyr Lys Thr Thr Pro Pro
                               165                    170                    175

Val Leu Asp Ser Asp Gly Ser Phe Phe Leu Ala Ser Ala Leu Thr Val
                               180                    185                    190

Asp Lys Ser Arg Trp Gln Gln Gly Asn Val Phe Ser Cys Ser Val Met
                               195                    200                    205

His Glu Ala Leu His Asn His Tyr Thr Gln Lys Ser Leu Ser Leu Ser
                               210                    215                    220

Pro Gly Lys
            225

<210> SEQ ID NO 32
<211> LENGTH: 471
<212> TYPE: PRT
<213> ORGANISM: artificial sequence
<220> FEATURE:
<223> OTHER INFORMATION: T366W +F405K +Y349D

<400> SEQUENCE: 32

Glu Val Gln Leu Leu Glu Ser Gly Gly Gly Val Val Gln Pro Gly Arg
             1               5                      10                     15

Ser Leu Arg Leu Ser Cys Ile Ala Ser Gly Phe Thr Phe Ser Ser Tyr
                                20                     25                     30

Pro Met Thr Trp Val Arg Gln Ala Pro Gly Lys Gly Leu Glu Trp Val
                                35                     40                     45

Ala Ser Ile Ser Tyr Asp Gly Ser Tyr Lys Tyr Lys Ala Asp Ser Met
                                50                     55                     60

Lys Gly Arg Leu Thr Ile Ser Arg Asp Asn Ser Lys Asn Thr Leu Tyr
             65                     70                     75                     80

Leu Glu Met Asn Ser Leu Thr Ala Glu Asp Thr Ala Val Tyr Tyr Cys
                                85                     90                     95

Ala Arg Thr Ala Phe Phe Asn Ala Tyr Asp Phe Trp Gly Gln Gly Thr
                               100                    105                    110

Leu Val Thr Val Ser Ser Ala Ser Thr Lys Gly Pro Ser Val Gly Gly
                               115                    120                    125

Gly Gly Ser Gly Gly Gly Gly Ser Glu Ile Val Met Thr Gln Ser Pro
```

```
            130                 135                 140
Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Asp Thr Leu Pro Pro Ser Arg Asp Glu Leu Thr Lys
    370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Lys Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 33
<211> LENGTH: 227
<212> TYPE: PRT
<213> ORGANISM: artificial sequence
<220> FEATURE:
<223> OTHER INFORMATION: T366S+L368A+Y407V +K409A +E357A

<400> SEQUENCE: 33

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
```

```
                    20                  25                  30
Ile Ser Arg Thr Pro Glu Val Thr Cys Val Val Val Asp Val Ser His
             35                  40                  45
Glu Asp Pro Glu Val Lys Phe Asn Trp Tyr Val Asp Gly Val Glu Val
         50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
             100                 105                 110
Glu Lys Thr Ile Ser Lys Ala Lys Gly Gln Pro Arg Glu Pro Gln Val
         115                 120                 125
Tyr Thr Leu Pro Pro Ser Arg Asp Ala Leu Thr Lys Asn Gln Val Ser
     130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                 165                 170                 175
Val Leu Asp Ser Asp Gly Ser Phe Phe Leu Val Ser Ala Leu Thr Val
             180                 185                 190
Asp Lys Ser Arg Trp Gln Gln Gly Asn Val Phe Ser Cys Ser Val Met
         195                 200                 205
His Glu Ala Leu His Asn His Tyr Thr Gln Lys Ser Leu Ser Leu Ser
     210                 215                 220
Pro Gly Lys
225

<210> SEQ ID NO 34
<211> LENGTH: 471
<212> TYPE: PRT
<213> ORGANISM: artificial sequence
<220> FEATURE:
<223> OTHER INFORMATION: T366W+F405K+Y349D+S354D

<400> SEQUENCE: 34

Glu Val Gln Leu Leu Glu Ser Gly Gly Gly Val Val Gln Pro Gly Arg
 1               5                  10                  15
Ser Leu Arg Leu Ser Cys Ile Ala Ser Gly Phe Thr Phe Ser Ser Tyr
             20                  25                  30
Pro Met Thr Trp Val Arg Gln Ala Pro Gly Lys Gly Leu Glu Trp Val
         35                  40                  45
Ala Ser Ile Ser Tyr Asp Gly Ser Tyr Lys Tyr Lys Ala Asp Ser Met
     50                  55                  60
Lys Gly Arg Leu Thr Ile Ser Arg Asp Asn Ser Lys Asn Thr Leu Tyr
 65                  70                  75                  80
Leu Glu Met Asn Ser Leu Thr Ala Glu Asp Thr Ala Val Tyr Tyr Cys
                 85                  90                  95
Ala Arg Thr Ala Phe Phe Asn Ala Tyr Asp Phe Trp Gly Gln Gly Thr
             100                 105                 110
Leu Val Thr Val Ser Ser Ala Ser Thr Lys Gly Pro Ser Val Gly Gly
         115                 120                 125
Gly Gly Ser Gly Gly Gly Gly Ser Glu Ile Val Met Thr Gln Ser Pro
     130                 135                 140
Ala Thr Leu Ser Val Ser Pro Gly Glu Arg Ala Thr Leu Ser Cys Arg
```

```
            145                 150                 155                 160
        Ala Ser Gln Ser Val Arg Ser Asn Leu Ala Trp Tyr Gln Gln Lys Pro
                        165                 170                 175

Gly Gln Ala Pro Arg Leu Leu Ile Tyr Ala Ala Ser Thr Arg Ala Thr
                        180                 185                 190

Gly Ile Pro Ala Arg Phe Ser Gly Ser Gly Ser Gly Thr Glu Phe Thr
                        195                 200                 205

Leu Thr Ile Ser Ser Leu Gln Ser Glu Asp Phe Ala Val Tyr Tyr Cys
                    210                 215                 220

Gln Gln Tyr Asn Glu Trp Phe Arg Thr Ser Gly Gln Gly Thr Lys Val
        225                 230                 235                 240

Glu Ile Lys Arg Asp Lys Thr His Thr Cys Pro Pro Cys Pro Ala Pro
                        245                 250                 255

Glu Leu Leu Gly Gly Pro Ser Val Phe Leu Phe Pro Pro Lys Pro Lys
                        260                 265                 270

Asp Thr Leu Met Ile Ser Arg Thr Pro Glu Val Thr Cys Val Val Val
                        275                 280                 285

Asp Val Ser His Glu Asn Pro Glu Val Lys Phe Asn Trp Tyr Val Asp
                    290                 295                 300

Gly Val Glu Val His Asn Ala Lys Thr Lys Pro Arg Glu Glu Gln Tyr
        305                 310                 315                 320

Asn Ser Thr Tyr Arg Val Val Ser Val Leu Thr Val Leu His Gln Asp
                        325                 330                 335

Trp Leu Asn Gly Lys Glu Tyr Lys Cys Lys Val Ser Asn Lys Ala Leu
                        340                 345                 350

Pro Ala Pro Ile Glu Lys Thr Ile Ser Lys Ala Lys Gly Gln Pro Arg
                        355                 360                 365

Glu Pro Gln Val Asp Thr Leu Pro Pro Asp Arg Asp Glu Leu Thr Lys
                    370                 375                 380

Asn Gln Val Ser Leu Trp Cys Leu Val Lys Gly Phe Tyr Pro Ser Asp
        385                 390                 395                 400

Ile Ala Val Glu Trp Glu Ser Asn Gly Gln Pro Glu Asn Asn Tyr Lys
                        405                 410                 415

Thr Thr Pro Pro Val Leu Asp Ser Asp Gly Ser Phe Lys Leu Tyr Ser
                        420                 425                 430

Lys Leu Thr Val Asp Lys Ser Arg Trp Gln Gln Gly Asn Val Phe Ser
                    435                 440                 445

Cys Ser Val Met His Glu Ala Leu His Asn His Tyr Thr Gln Lys Ser
        450                 455                 460

Leu Ser Leu Ser Pro Gly Lys
        465                 470

<210> SEQ ID NO 35
<211> LENGTH: 354
<212> TYPE: PRT
<213> ORGANISM: artificial sequence
<220> FEATURE:
<223> OTHER INFORMATION: VhH-Fc fusion protein

<400> SEQUENCE: 35

Gln Val Gln Leu Gln Glu Ser Gly Gly Gly Ser Val Gln Ala Gly Gly
1               5                   10                  15

Ser Leu Arg Leu Ser Cys Ala Ala Ser Glu Tyr Ile Tyr Ser Ser Tyr
                20                  25                  30

Cys Met Ala Trp Phe Arg Gln Ala Pro Gly Lys Glu Arg Glu Gly Val
```

35                  40                  45
Ala Val Ile Gly Ser Asp Gly Ser Thr Ser Tyr Ala Asp Ser Val Lys
 50                  55                  60

Gly Arg Phe Thr Ile Ser Lys Asp Asn Ala Lys Asn Thr Leu Tyr Leu
 65                  70                  75                  80

Gln Met Asn Ser Leu Lys Pro Glu Asp Thr Ala Met Tyr Tyr Cys Ala
                 85                  90                  95

Ala Ile Gly Gly Tyr Cys Tyr Gln Pro Pro Tyr Glu Tyr Gln Tyr Trp
            100                 105                 110

Gly Gln Gly Thr Gln Val Thr Val Ser Ser Glu Pro Lys Ser Ser Asp
        115                 120                 125

Lys Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys

<210> SEQ ID NO 36
<211> LENGTH: 1121
<212> TYPE: DNA
<213> ORGANISM: artificial sequence
<220> FEATURE:
<223> OTHER INFORMATION: VhH-Fc encoding genes

<400> SEQUENCE: 36
atggagaccg acaccctgct gctgtgggtg ctgctgctgt gggtgcccgg cagcaccggc     60
caggtgcagc tgcaggagtc tgggggaggc tcggtgcagg ctggagggtc tctgagactc    120
tcctgtgcag cctctgaata catctacagt agctactgca tggcctggtt ccgccaggct    180
ccagggaagg agcgcgaggg ggtcgcagtt attgggagtg atggtagcac aagctacgca    240

```
gactccgtga aaggccgatt caccatctcc aaagacaacg ccaagaacac tctgtatctg    300
caaatgaaca gcctgaaacc tgaggacact gccatgtact actgtgcggc catcggtggt    360
tactgctacc aaccaccta  tgagtaccag tactggggcc aggggaccca ggtcaccgtc    420
tcccagaacc gaaaagcagc gacaagaccc acacctgccc ccctgcccc  gcccccgagc    480 tgctgggcgg ccccagcgtg ttcctgttcc cccccaagcc caaggacacc ctgatgatca    540
gccgcacccc cgaggtgacc tgcgtggtgg tggacgtgag ccacgagaac ccgaggtga     600 agttcaactg gtacgtggac ggcgtggagg tgcacaacgc caagaccaag ccccgcgagg    660
agcagtacaa cagcacctac cgcgtggtga gcgtgctgac cgtgctgcac caggactggc    720
tgaacggcaa ggagtacaag tgcaaggtga gcaacaaggc cctgccc gcc cccatcgaga   780 agaccatcag caaggccaag ggccagcccc gcgagcccca ggtgtacacc ctgccccca    840 gccgcgacga gctgaccaag aaccaggtga gcctgacctg cctggtgaag ggcttctacc    900
ccagcgacat cgccgtggag tgggagagca acggccagcc cgagaacaac tacaagacca    960
ccccccccgt gctggacagc gacggcagct tcttcctgta cagcaagctg accgtggaca   1020
agagccgctg gcagcagggc aacgtgttca gctgcagcgt gatgcacgag gccctgcaca   1080
accactacac ccagaagagc ctgagcctga gccccggcaa g                       1121
```

HETERODIMER MOLECULE BASED ON CH3 DOMAIN, AND PREPARATION METHOD AND USE THEREOF

TECHNICAL FIELD

The present disclosure relates to the field of antibody engineering, and in particular, provides a heterodimer molecule based on CH3 domain, and preparation method and use thereof.

INCORPORATION BY REFERENCE OF SEQUENCE LISTING

The Sequence Listing in an ASCII text file, named 36019_US_Sequence_Listing.txt of 103 KB, created on May 31, 2018, and submitted to the United States Patent and Trademark Office via EFS-Web, is incorporated herein by reference.

BACKGROUND

In recent 15 years, monoclonal antibody drugs have rapidly developed, becoming a growing point in the pharmaceutical industry. Since 1996, about 30 monoclonal antibody drugs have been approved to come into the market, among which 9 monoclonal antibody drugs obtain annual sales of more than USD 1 billion. In 2010, the total sales of monoclonal antibody drugs were more than USD 30 billion with the annual average growth rate of more than 10%. A monoclonal antibody exhibits strong target specificity, and therefore can only inhibit a single target site. However, for many diseases, including tumors, autoimmune diseases, etc., it is necessary to inhibit multiple signaling pathways to avoid compensatory effects. For viral infection diseases, due to high mutation rate of viruses, it is usually necessary to inhibit a plurality of antigen sites to avoid escape. In addition, bifunctional antibodies and proteins are used to specifically activate the human immune system (Wolf, Hofmeister et al. 2005).

It is well known that the crystallizable fragments (Fc) of an antibody form a homodimer, and plays a key role in maintaining the in vivo stability of the antibody and Fc fusion protein. Modifying Fc to form a heterodimer is an effective method to produce a multifunctional antibody, protein and maintain in vivo stability thereof.

A typical application example of a heterodimer is a bispecific antibody (BsAbs), which is an immunoglobulin molecule containing two different ligand binding sites. A bispecific antibody is active to at least two different antigens (Carter 2001). It replaces the form of two identical Fab arms in a classic antibody with the form of two Fab arms with different sequences. Therefore, two Y type arms can bind to different antigens. The application of bispecific antibodies in treating cancers has been summarized by many literatures (Carter 2001; Chames and Baty 2009; Chames and Baty 2009).

There is no bispecific antibody in a natural state, which can be prepared only by a special method. The prior preparation methods of bispecific antibodies include chemical crosslinking, hybridizing F(ab')2 molecules, murine hybridoma method, etc. For bispecific antibodies produced by the chemical crosslinking method, they exhibit heterogenicity, instability of products between batches, and the characteristic thereof that antibody specificity can be easily changed by some modifications or improper bindings, thus they are not suitable for use in vivo. A bispecific hybrid molecule produced from a mercapto-crosslinked proteinase digestion fragment F(ab') has a relatively homogeneous ingredient, but the preparation process is time-consuming and labor-consuming with a very low yield. Bispecific antibodies produced by the hybridoma method have a reliable source, but randomly pairing between light chains and heavy chains will produce a plurality of possible antibody forms, making the production and purification of bispecific antibodies very difficult as a result.

As early as in the 1990s, Carter et al. modified some amino acids in heavy chains of antibodies by a "knob into hole" model, and relatively successfully achieved the preparation of bispecific antibodies (Ridgway, Presta et al. 1996; Carter 2001). The "knob into hole" model was originally proposed by Crick to solve the problem of amino acid side chain folding between adjacent α-spirals (Crick 1952). Carter et al. created a "knob" by mutating an amino acid with a short side chain in a CH3 region of a first heavy chain of the Fc region into an amino acid with a long side chain (e.g., T366Y), and created "holes" by mutating some amino acids in a CH3 region of a second heavy chain into amino acids with short side chains (Y407T, et al.) The principle of the "knob into hole" model is that the interaction of "knob into hole" supports the heterodimer formation, while the "knob-knob" model and "hole-hole" model hinder the homodimer formation. They further introduced a disulfide bond into the CH3 region on the basis of the "knob into hole" mutation to strengthen the binding capacity of the heterodimer. However, in their research results, the "hole-hole" model still did not have enough ability to hinder the homodimer formation. Later, the research group tried to further enhance the heterodimer content by random mutation-bacteriophage display and other methods, but still did not solve the essential issues. In order to enhance the proportion of heterodimer, some researchers prepared heterodimers by respectively preparing two antibodies and intermolecular disulfide bond reducing-repairing in vitro, but the preparation process is obviously too complex.

Therefore, it is still necessary to find suitable mutations in this field to further enhance the formation of heterodimer proteins and decrease the formation of homodimer proteins.

SUMMARY OF INVENTION

By comprehensively considering various interactions between interfacial amino acids, for example, an ionic action, a hydrophobic interaction and a spatial action, the invention according to the present disclosure has obtained an optimal CH3 mutant sequence, which is more inclined to form a heterodimer rather than a homodimer, thereby greatly improving the yield of the heterodimer molecule.

In a respect, the present disclosure relates to a heterodimer molecule, comprising a first polypeptide chain and a second polypeptide chain, wherein said first polypeptide chain comprises a first CH3 domain of an antibody heavy chain constant region, said second polypeptide chain comprises a second CH3 domain of an antibody heavy chain constant region, and comparing to a corresponding wild-type CH3 domain of a human antibody heavy chain constant region, said first CH3 domain and said second CH3 domain comprise an amino acid mutation selected from the following groups (1) to (3):

(1) an amino acid mutation at Y349 and T366 of said first CH3 domain, and an amino acid mutation at D356, T366, L368 and Y407 of said second CH3 domain, and said first CH3 domain and/or said second CH3 domain further comprise an amino acid mutation at 1-3 residues selected from the group consisting of F405, K409, K360, Q347 and L368;

(2) an amino acid mutation at T366 and K409 of said first CH3 domain, and an amino acid mutation at T366, L368, Y407 and F405 of said second CH3 domain, and optionally said first CH3 domain and/or said second CH3 domain further comprise an amino acid mutation at 1-2 residues selected from the group consisting of K392, D399, Y349, 5354 and E357; and (3) an amino acid mutation at T366 and F405 of said first CH3 domain, and an amino acid mutation at T366, L368, Y407 and K409 of said second CH3 domain, and optionally said first CH3 domain and/or said second CH3 domain further comprise an amino acid mutation at 1-2 residues selected from the group consisting of K392, D399, Y349, 5354 and E357;

wherein said amino acid is numbered according to the EU index of the KABAT numbering of the antibody Fc region.

In some embodiments, said first CH3 domain and said second CH3 domain comprise said amino acid mutation selected from said group (2) or (3), but do not comprise mutation Y349C or D356C.

In some embodiments, said first CH3 domain and/or said second CH3 domain further comprise a mutation selected from the following groups:

1a) a mutation at F405 of said second CH3 domain;
1b) a mutation at F405 of said first CH3 domain;
1c) a mutation at K409 of said first CH3 domain, and a mutation at F405 of said second CH3 domain;
1d) a mutation at F405, K360 and Q347 of said first CH3 domain, and a mutation at Q347 of said second CH3 domain;
1e) a mutation at F405 and Q347 of said first CH3 domain, and a mutation at K360 and Q347 of said second CH3 domain;
1f) a mutation at K409, K360 and Q347 of said first CH3 domain, and a mutation at F405 and Q347 of said second CH3 domain;
1g) a mutation at K409 and Q347 of said first CH3 domain, and a mutation at F405, K360 and Q347 of said second CH3 domain; and
1h) a mutation at K409 and L368 of said first CH3 domain, and a mutation at F405 of said second CH3 domain.

In some embodiments, said first CH3 domain and/or said second CH3 domain optionally further comprise a mutation selected from the following groups:

2a) a mutation at K392 of said first CH3 domain and a mutation at D399 of said second CH3 domain;
2b) a mutation at Y349 of said first CH3 domain and a mutation at E357 of said second CH3 domain; and
2c) a mutation at Y349 and 5354 of said first CH3 domain, and a mutation at E357 of said second CH3 domain.

In some embodiments, said first CH3 domain and/or said second CH3 domain optionally further comprise a mutation selected from the following groups:

3a) a mutation at D399 of said first CH3 domain and a mutation at K392 of said second CH3 domain;
3b) a mutation at Y349 of said first CH3 domain and a mutation at E357 of said second CH3 domain; and
3c) a mutation at Y349 and S354D of said first CH3 domain and a mutation at E357 of said second CH3 domain.

In some embodiments, said amino acid mutations are independently selected from: a mutation from a non-charged amino acid to a charged amino acid, a mutation from a charged amino acid to a non-charged amino acid, or a mutation from a charged amino acid to an oppositely charged amino acid.

In some embodiments, said mutation in said first CH3 structural domain and/or said second CH3 structural domain comprises one or more mutations selected from the following group consisting of: Y349C, Y349D, D356C, T366W, T366S, L368A, L368E, L368G, F405K, Y407V, Y407A, K409E, K409A, K360E, Q347E, Q347R, K392D, D399S, E357A and S354D. For example, the mutation may be one or more mutations selected from the following mutations: Y349C, Y349D, D356C, T366W, T366S, L368A, L368E, L368G, F405K, Y407V, Y407A, K409E, K409A, K360E, Q347E, Q347R, K392D, D399S, E357A and S354D.

In some embodiments, said first CH3 domain comprises a mutation at one or more residues (e.g., at least one residue, at least two residues, at least three residues, at least four residues, at least five residues, at least six residues, at least seven residues, or at least eight residues) selected from the group consisting of: Y349, T366, F405, K409, L368, K392, 5354 and D399.

In some embodiments, said second CH3 domain comprises a mutation at one or more residues (e.g., at least one residue, at least two residues, at least three residues, at least four residues, at least five residues, at least six residues, at least seven residues, at least eight residues or at least nine residues) selected from the group consisting of: D356, T366, L368, Y407, F405, D399, E357, K409 and K392.

In some embodiments, said first CH3 domain comprises a mutation at one or more residues (e.g., at least one residue, at least two residues, at least three residues, at least four residues, at least five residues, at least six residues, at least seven residues, or at least eight residues) selected from the group consisting of: Y349, T366, F405, K409, L368, K392, 5354 and D399; and said second CH3 domain comprises a mutation at one or more residues (e.g., at least one residue, at least two residues, at least three residues, at least four residues, at least five residues, at least six residues, at least seven residues, at least eight residues or at least nine residues) selected from the group consisting of: D356, T366, L368, Y407, F405, D399, E357, K409 and K392.

In some embodiments, said first CH3 domain comprises one or more mutations (e.g., at least one mutation, at least two mutations, at least three mutations, at least four mutations, at least five mutations, at least six mutations, at least seven mutations, at least eight mutations or at least nine mutations) selected from the group consisting of: Y349C, T366W, F405K, K409A, L368E, K392D, Y349D, S354D and D399S.

In some embodiments, said second CH3 domain comprises one or more mutations (e.g., at least one mutation, at least two mutations, at least three mutations, at least four mutations, at least five mutations, at least six mutations, at least seven mutations, at least eight mutations, at least nine mutations, at least ten mutations, or at least eleven mutations) selected from the group consisting of: D356C, T366S, L368A, Y407V, F405K, D399S, L368G, Y407A, E357A, K409A and K392D.

In some embodiments, said first CH3 domain comprises one or more mutations (e.g., at least one mutation, at least two mutations, at least three mutations, at least four mutations, at least five mutations, at least six mutations, at least seven mutations, at least eight mutations or at least nine mutations) selected from the group consisting of: Y349C, T366W, F405K, K409A, L368E, K392D, Y349D, S354D and D399S; and said second CH3 domain comprises one or more mutations (e.g., at least one mutation, at least two mutations, at least three mutations, at least four mutations, at least five mutations, at least six mutations, at least seven mutations, at least eight mutations or at least nine mutations)

selected from the group consisting: D356C, T366S, L368A, Y407V, F405K, D399S, L368G, Y407A, E357A, K409A and K392D.

In some embodiments, said first CH3 domain and said second CH3 domain comprise one group of mutations selected from the following groups:

1) said first CH3 domain: Y349C+T366W, said second CH3 domain: D356C+T366S+L368A+Y407V+F405K;

2) said first CH3 domain: Y349C+T366W+F405K, said second CH3 domain: D356C+T366S+L368A+Y407V;

3) said first CH3 domain: Y349C+T366W+K409E, said second CH3 domain: D356C+T366S+L368A+Y407V+F405K;

4) said first CH3 domain: Y349C+T366W+K409A, said second CH3 domain: D356C+T366S+L368A+Y407V+F405K;

5) said first CH3 domain: Y349C+T366W+F405K+K360E+Q347E, said second CH3 domain: D356C+T366S+L368A+Y407V+Q347R;

6) said first CH3 domain: Y349C+T366W+F405K+Q347R, said second CH3 domain: D356C+T366S+L368A+Y407V+K360E+Q347E;

7) said first CH3 domain: Y349C+T366W+K409A+K360E+Q347E, said second CH3 domain: D356C+T366S+L368A+Y407V+F405K+Q347R;

8) said first CH3 domain: Y349C+T366W+K409A+Q347R, said second CH3 domain: D356C+T366S+L368A+Y407V+F405K+K360E+Q347E;

9) said first CH3 domain: Y349C+T366W+K409A+L368E, said second CH3 domain: D356C+T366S+L368A+Y407V+F405K;

10) said first CH3 domain: T366W+K409A+K392D, said second CH3 domain: T366S+L368A+Y407V+D399S+F405K;

11) said first CH3 domain: T366W+K409A, said second CH3 domain: T366S+L368G+Y407A+F405K;

12) said first CH3 domain: T366W+K409A+Y349D, said second CH3 domain: T366S+L368A+Y407V+F405K+E357A;

13) said first CH3 domain: T366W+K409A+Y349D+S354D, said second CH3 domain: T366S+L368A+Y407V+F405K+E357A;

14) said first CH3 domain: T366W+F405K, said second CH3 domain: T366S+L368A+Y407V+K409A;

15) said first CH3 domain: T366W+F405K+D399S, said second CH3 domain: T366S+L368A+Y407V+K409A+K392D;

16) said first CH3 domain: T366W+F405K, said second CH3 domain: T366S+L368G+Y407A+K409A;

17) said first CH3 domain: T366W+F405K+Y349D, said second CH3 domain: T366S+L368A+Y407V+K409A+E357A; and 18) said first CH3 domain: T366W+F405K+Y349D+S354D, said second CH3 domain: T366S+L368A+Y407V+K409A+E357A.

In some embodiments, said first CH3 domain and said second CH3 domain contain one group of mutations selected from the following groups:

2) said first CH3 domain: Y349C+T366W+F405K, said second CH3 domain: D356C+T366S+L368A+Y407V;

4) said first CH3 domain: Y349C+T366W+K409A, said second CH3 domain: D356C+T366S+L368A+Y407V+F405K;

9) said first CH3 domain: Y349C+T366W+K409A+L368E, said second CH3 domain: D356C+T366S+L368A+Y407V+F405K;

10) said first CH3 domain: T366W+K409A+K392D, said second CH3 domain: T366S+L368A+Y407V+D399S+F405K;

11) said first CH3 domain: T366W+K409A, said second CH3 domain: T366S+L368G+Y407A+F405K;

13) said first CH3 domain: T366W+K409A+Y349D+S354D, said second CH3 domain: T366S+L368A+Y407V+F405K+E357A;

15) said first CH3 domain: T366W+F405K+D399S, said second CH3 domain: T366S+L368A+Y407V+K409A+K392D;

16) said first CH3 domain: T366W+F405K, said second CH3 domain: T366S+L368G+Y407A+K409A; and 18) said first CH3 domain: T366W+F405K+Y349D+S354D, said second CH3 domain: T366S+L368A+Y407V+K409A+E357A.

In some embodiments, said first polypeptide chain and said second polypeptide chain further comprise a CH2 domain of an antibody heavy chain constant region, respectively. In some embodiments, the said CH2 domain is located at the N-terminal of the CH3 domain, and is linked directly or through a linker peptide to the N-terminal of the CH3 domain.

In some embodiments, said first polypeptide chain and said second polypeptide chain further comprise a hinge region of an antibody heavy chain constant region or a part thereof, respectively. In some embodiments, said part of said hinge region is D221-P230.

In some embodiments, said hinge region or a part thereof is located at the N-terminal of the CH3 domain. And when there is a said CH2 domain, said hinge region or a part thereof is further located at the N-terminal of the CH2 domain, and is linked directly or through a linker peptide to the CH2 or CH3 domain.

In some embodiments, said wild-type CH3 domain of the human antibody heavy chain constant region is selected from the group consisting of a CH3 domain of a human IgG (e.g., IgG1, IgG2, IgG3 or IgG4) heavy chain constant region, a CH3 domain of a human IgA (e.g., IgA1, IgA2) heavy chain constant region, a CH3 domain of a human IgD heavy chain constant region, a CH3 domain of a human IgE heavy chain constant region and a CH3 domain of a human IgM heavy chain constant region.

In some embodiments, said wild-type CH3 domain of the human antibody heavy chain constant region is a CH3 domain of a human IgG1 heavy chain constant region.

In some embodiments, said first polypeptide chain and/or said second polypeptide chain further comprise a molecule binding region, and said molecule binding region is selected from the group consisting of an antigen binding region, a receptor binding region and an enzyme binding region. In some embodiments, said antigen binding region comprises an antibody variable region.

In some embodiments, said heterodimer molecule is a bispecific antibody, a bispecific fusion protein or an antibody-fusion protein chimera.

In another respect, the present disclosure relates to a composition (e.g., a pharmaceutical composition), comprising the heterodimer molecule according to the present disclosure, and optionally a pharmaceutically acceptable carrier or excipient.

In another respect, the present disclosure provides a nucleic acid molecule, encoding said first polypeptide chain or said second polypeptide chain of the heterodimer molecule according to the present disclosure, or encoding said first polypeptide chain and said second polypeptide chain of the heterodimer molecule according to the present disclosure.

In another respect, the present disclosure provides a vector, comprising the nucleic acid molecule according to the present disclosure.

In another respect, the present disclosure provides a host cell, comprising the vector according to the present disclosure.

In another respect, the present disclosure provides a use of the heterodimer molecule, the composition, the nucleic acid, the vector or the host cell in the manufacture of a bispecific antibody, a bispecific fusion protein or an antibody-fusion protein chimera according to the present disclosure.

In another respect, the present disclosure provides a method for preparing a heterodimer molecule, comprising expressing the heterodimer molecule using the host cell according to the present disclosure.

In some embodiments of said method for preparing a heterodimer molecule, the host cell comprises a vector encoding said first polypeptide chain and said second polypeptide chain of the heterodimer molecule, and the method comprises expressing, recovering and obtaining the heterodimer molecule using the host cell.

In some embodiments of said method for preparing a heterodimer molecule, the host cell comprises a first group of cells comprising a vector encoding said first polypeptide chain of the heterodimer molecule, a second group of cells comprises a vector encoding said second polypeptide chain of the heterodimer molecule, and the method comprises expressing said first polypeptide chain in said first group of cells to form a homodimer of said first polypeptide chain, expressing said second polypeptide chain in said second group of cells to form a homodimer of said second polypeptide chain, and then mixing the homodimer of said first polypeptide chain with the homodimer of said second polypeptide chain under a condition to form the heterodimer molecule. In some embodiments, said method further comprises reducing the homodimer of said first polypeptide chain and the homodimer of said second polypeptide chain to monomers, mixing and oxidizing the monomers, and then purifying the obtained heterodimer molecule. In some embodiments, said host cell comprises a vector encoding said first polypeptide chain and said second polypeptide chain of the heterodimer molecule, said first polypeptide chain and said second polypeptide chain are expressed respectively in two said host cells to form a homodimer of said first polypeptide chain and a homodimer of said second polypeptide chain, and then reducing, mixing, oxidizing and purifying the homodimer of said first polypeptide chain and the homodimer of said second polypeptide chain under a proper condition to obtain said heterodimer molecule.

In some embodiments of said method for preparing a heterodimer molecule, said first group of cells and said second group of cells were transfected with a construct or vector which comprises said first polypeptide chain or said second polypeptide chain, respectively. Said transfection may be transient transfection. For said transfection, the molar ratio of said construct or vector comprising said first polypeptide chain to said construct or vector comprising said second polypeptide chain may be 1:4 to 4:1, for example, 1:2 to 2:1, for example, about 1:1.

Additional aspects and advantages of the present disclosure will become readily apparent to those skilled in this art from the following detailed description, wherein only illustrative embodiments of the present disclosure are shown and described. Numerous modifications of the embodiments of the disclosure described herein will now occur to those skilled in the art without departing from the disclosure. Accordingly, the drawings and description of the present disclosure are to be regarded as illustrative in nature, but not as restrictive.

BRIEF DESCRIPTION OF THE DRAWINGS

FIG. 4A shows the interaction between the mutation F405K-K409A and nearby interfacial amino acids when a new mutation F405K-K409A is introduced. FIG. 4B shows the interaction change caused by the introduction of a new mutation.

DETAILED DESCRIPTION

Figure 1:
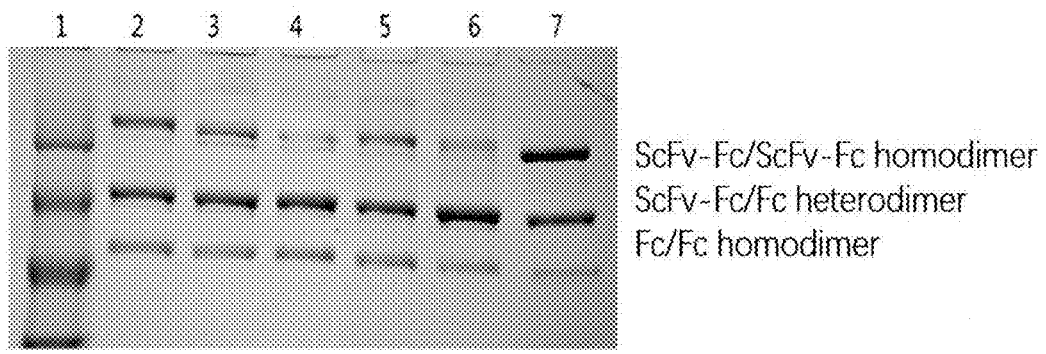
FIG. 1 shows the electrophoretic analysis result of transiently expressed ScFv-Fc/Fc heterodimer. 4% to 12% SDS-PAGE protein gel electrophoresis was used. Lanes 1 to 7 are successively: protein molecular mass markers; mutation combination KH, mutation combination 1, mutation combination 2, mutation combination 3, mutation combination 4 and a wild-type negative control combination. The homodimer and the heterodimer of products in each combination exhibit different migration distances in the gel electrophoresis due to molecular weight differences. The sites of different homodimer and heterodimer proteins are indicated in the FIG. 1.

The embodiments of the invention are illustrated in conjunction with the specific embodiments below, and those skilled in the art can understand other advantages and functions of the invention through the contents disclosed in the description.

In the present disclosure, both of said first polypeptide chain and said second polypeptide chain comprise a CH3 domain of an antibody Fc region, and the said two polypeptide chains interact with each other through the CH3 domain or the Fc region which comprises the CH3 domain to form a dimer, especially a heterodimer. Two polypeptide chains of the heterodimer may be different combinations.

For example, said first polypeptide chain is an antibody and said second polypeptide chain is a fusion protein, or both of the two polypeptide chains are fusion protein, or both of two polypeptide chains is an antibody (e.g., antibodies targeting to different antigen or antigen epitope). When the fusion protein comprises an antibody Fc region and an extracellular domain of a cell adhesion molecule, it is also known as an immune adhesin. Said cell adhesion molecule mainly refers to a molecule capable of identifying specific ligand cell surface receptor, for example, comprising cadherin, selectin, immunoglobulin superfamily, integrin and hyaladherin.

In the present disclosure, said CH3 domain is derived from a Fc region of an antibody, e.g., from a Fc region of human antibody (e.g., a Fc region of a human antibody heavy chain constant region). In some embodiments, said CH3 domain is derived from a Fc region of a human immunoglobulin (Ig) heavy chain constant region, e.g., from a Fc region of a heavy chain constant region of IgM, IgG (e.g., IgG1, IgG2, IgG3, IgG4), IgA (e.g., IgA1, IgA2), IgE and/or IgD. In some embodiments, said CH3 domain (e.g., a wild-type CH3 domain of human antibody heavy chain constant region) is derived from wild-type IgG1 of human, e.g., a wild-type CH3 domain of a human IgG1 antibody heavy chain constant region. In general, said CH3 domain of the Fc region of human antibody is derived from a corresponding wild-type Fc region of human antibody. A wild-type human antibody Fc region refers to an antibody Fc region in a natural human population, e.g., a Fc region of human antibody that is not artificially induced or artificially modified. In some embodiments, the Fc region of human antibody according to the present disclosure also comprises particular amino acid mutation of a corresponding wild-type human antibody Fc sequence, e.g., comprising amino acid mutations at a glycosylation site or other nonsense mutations, and also comprising particular amino acid mutations including according to the "knob-hole" model. For example, for CH3 and CH2 domains, except for mutations mentioned in the present disclosure, there may also be other mutations that do not affect the functions of antibodies (especially Fc region).

In the present disclosure, when the first polypeptide chain and/or the second polypeptide chain comprise a hinge region, said hinge region is linked between the two polypeptide chains as a flexible chain to ensure the functions of each polypeptide chain. Those skilled in the art can select the length of the hinge region as required, for example, selecting a full-length sequence or a part of the sequence thereof.

In the present disclosure, said amino acid of said Fc region or CH2, CH3 domain or hinge region is numbered according to the EU index of the Kabat numbering. As is known to those skilled in the art, even if said amino acid insertions or deletions or other mutations lead to a change of the amino acid sequences in the above regions, site numbers of the amino acids determined according to the standard sequences of EU index of the Kabat numbering remain unchanged.

In the present disclosure, a human antibody heavy chain constant region may comprise a combination of two or more domains in CH1, CH2, CH3 and CH4 domain in heavy chains with an antibody hinge region. In some embodiments, said human antibody Fc region comprises at least one antibody hinge region, one CH2 domain and one CH3 domain. In some embodiments, said CH2 domain is a CH2 domain of a human IgG1 heavy chain constant region, which corresponds to amino acids 228-340 according to the EU index numbering system. In some embodiments, the CH2 domain corresponds to a corresponding region of any other isotypic antibody described in the present disclosure. In some embodiments, said CH3 domain is a CH3 domain of a human IgG1 heavy chain constant region, which corresponds to amino acids 341-447 according to the EU index numbering system. In some embodiments, the CH3 domain corresponds to a corresponding region of any other isotypic antibody described in the present disclosure.

In the present disclosure, the charged amino acid comprises arginine, lysine, aspartic acid and glutamic acid.

In the present disclosure, the heterodimer molecule can be purified from a host cell using a standard experimental method. For example, when a heterodimer protein comprises a Fc region of an antibody, it can be purified using protein A. The purification method comprises, but not limited to, a chromatographic technique, such as size exclusion, ion exchange, affinity chromatography and ultrafiltration, or an appropriate combination of the methods thereof.

In the present disclosure, the EU index is described in, e.g., Kabat, etc., *Sequences of Proteins of Immunological Interest, Public Health Service* 5th edition, National Institutes of Health, Bethesda, Md. (1991).

In the present disclosure, by comprehensively considering various interactions between interfacial amino acids, for example, an ionic action, a hydrophobic interaction and a spatial action, a preferred CH3 mutant sequence being more inclined to form a heterodimer rather than a homodimer was screened, thereby greatly enhancing the yield of the heterodimer molecule. Furthermore, in some embodiments of the present disclosure, a heterodimer protein crystal comprising a Fc region was prepared, and the crystal structure was analyzed and a three-dimensional structure model was established to further understand the direct interaction between interfacial amino acids, and the previous view that a stable disulfide bond is bound to be formed between two cysteines on Y349C and D356C was abandoned. A mutation combination formed on this basis is more inclined to form heterodimers, rather than homodimers, thus greatly reducing the proportion of homodimers while greatly enhancing the proportion of heterodimers.

The embodiments of the application according to the present disclosure will be described below in detail in conjunction with the examples, but those skilled in the art will understand that such examples are exemplary only and it is not intended that the invention be limited by the specific examples provided within the specification. The specific conditions which were not indicated in the specific examples, are in accordance with general conditions or conditions recommended by the manufacturer. The reagents or equipment which did not indicate manufacturers, are conventional products which can be obtained from the market.

Example 1: Acquisition of First Round Mutation Combination Candidate

1. Modeling of Fc Domain and Acquisition of an Interfacial Amino Acid

A total of 48 crystal structures of human IgG1 antibody comprising a Fc domain were acquired from Protein Database (PDB, www.pdb.org), and a structural similarity search algorithm (Reference: Yuzhen Ye and Adam Godzik. FATCAT: a web server for flexible structure comparison and structure similarity searching. Nucleic Acids Res., 2004, 32 (Web Server issue): W582-585.) was used to conclude that the Fc regions of the 48 antibodies were derived from 1DN2 (PDB number).

Amino acid contact between CH3-CH3 domain of antibodies (PDB No.: 1DN2) was screened and identified based on amino acid interaction distance using CMA software (website: http://ligin.weizmann.ac.il/cma/) which can identify contact amino acids of proteins. According to the amino acid contact regulation, an interfacial amino acid refers to an amino acid with the distance between a heavy atom on a side chain and a heavy atom of any one amino acid on the other chain less than a threshold value. In this example, the threshold value is 4.5 Å, and may also be 5.5 Å (e.g., manuscript: B. Erman, I. Bahar and R. L. Jernigan. Equilibrium states of rigid bodies with multiple interaction sites. Application to protein helices. J. Chem. Phys. 1997, 107: 2046-2059.). The conservative conditions of the contact interface between human and mouse IgG subtype amino acids can be obtained through multiple sequence alignment. Table 1 shows 34 interfacial amino acids of an antibody 1DN2 screened by amino acid contact (that is, the distance between two amino acid molecules is less than 4.5 Å), where chain A and chain B represent a first chain and a second chain of the antibody 1DN2, respectively. The following amino acid was numbered according to the EU index of the KABAT numbering of the antibody Fc region.

TABLE 1

List of CH3—CH3 Interfacial Amino Acids of Antibody 1DN2

| Contacting amino acids in chain A | Contacting amino acids in chain B |
|---|---|
| Gln347 | Lys360 |
| Val348 | Glu356 |
| Tyr349 | Ser354, Glu356, Glu357, Lys360 |
| Thr350 | Ser354, Glu356 |
| Leu351 | Leu351, Pro352, Pro353, Ser354, Thr366 |
| Pro352 | Leu351, Pro352 |
| Pro353 | Leu351 |
| Ser354 | Tyr349, Thr350, Leu351 |
| Glu356 | Val348, Tyr349, Thr350, Lys439 |
| Glu357 | Tyr349, Leu368, Lys370 |
| Lys360 | Gln347, Tyr349, Lys370 |
| Gln362 | Lys370 |
| Val363 | Lys370 |
| Ser364 | Leu368, Lys370, Tyr407 |
| Leu365 | Tyr407 |
| Thr366 | Leu351, Leu368, Tyr407 |
| Leu368 | Glu357, Ser364, Thr366, Lys409 |
| Lys370 | Glu357, Lys360, Gln362, Ser364, Lys409, Thr411 |
| Asn390 | Ser400 |
| Lys392 | Val397, Leu398, Asp399, Ser400, Phe405 |
| Thr393 | Val397 |
| Thr394 | Thr394, Val397, Phe405, Tyr407 |
| Pro395 | Pro395, Val397 |
| Val397 | Lys392, Thr393, Thr394, Pro395 |
| Leu398 | Lys392 |
| Asp399 | Lys392, Lys409, Thr411 |
| Ser400 | Asn390, Lys392 |
| Phe405 | Lys392, Thr394, Tyr407, Lys409 |
| Leu406 | Thr394 |
| Tyr407 | Thr366, Thr394, Phe405, Tyr407, Lys409 |
| Ser408 | Tyr407 |

TABLE 1-continued

List of CH3—CH3 Interfacial Amino Acids of Antibody 1DN2

| Contacting amino acids in chain A | Contacting amino acids in chain B |
|---|---|
| Lys409 | Leu368, Lys370, Asp399, Phe405, Tyr407 |
| Thr411 | Lys370, Asp399 |
| Lys439A | Glu356B |

2. Mutating Amino Acids to Change Ionic Action

According to the results of Table 1, an amino acid pair containing a charged amino was selected from said contacting amino acid pairs, and one amino on one chain therein was mutated (a non-charged amino acid became a charged amino acid, or a charged amino acid became a non-charged amino acid, or a charged amino acid became oppositely charged), so that the ionic action between a Fc chain A and a Fc chain B was unbalanced, thus the probability of homodimer formation was decreased, and/or the heterodimer was increased.

As an example, e.g., Phe405 of chain A was mutated to Phe405Lys (may also be written as F405K), and chain B remained unchanged. Because the contacting amino acid residue on the chain B, which was around 405th amino acid residue comprised two Lys, both of which were positively charged amino acids, when a chain A paired with a chain A, positive charges carried by an F405K mutation on the two chains would introduce a great repulsive force; while when a chain A paired with a chain B, only one chain (chain A) exhibited the repulsive force introduced by the F405K mutation, and the other chain (chain B) maintained as Phe405 without introducing a repulsive force. Under this condition, there was very significant mutual repulsion between two chains A, which is much greater than the mutual repulsion between the chain A and the chain B or between the two chains B, and therefore can effectively reduce the formation of AA homodimer.

If a F405K mutation was introduced into a chain A and the contacting amino acid residue Lys409 on a chain B corresponding to the F405K mutation residue on the chain A was mutated to K409E or K409A, then when a chain A paired with a chain A, positive charges introduced by the F405K mutation on the two chains A will still introduce a great repulsive force; when a chain A paired with a chain B, the F405k mutation on the chain A interacted with the K409E or K409A mutation on the chain B without a repulsive force, or even with an attractive force (K409E); and when a chain B paired with a chain B, neither repulsive force nor attractive force was introduced. Under this condition, there was very significant mutual repulsion between the two chains A, and the repulsive force between the chain A and the chain B was reduced or an attractive force was introduced between the chain A and the chain B, which can therefore effectively reduce the formation of AA homodimer, and promote the formation of AB heterodimer at the same time.

Similarly, mutation combinations obtained in this example are shown in the table below:

TABLE 2

List of Mutation Combinations of Heterodimers

| Combination | Fc chain | Mutation | Corresponding SEQ ID NO |
|---|---|---|---|
| KH | A | Y349C + T366W | 6 |
|  | B | D356C + T366S + L368A + Y407V | 7 |
| 1 | A | Y349C + T366W | 6 |
|  | B | D356C + T366S + L368A + Y407V + F405K | 8 |

TABLE 2-continued

List of Mutation Combinations of Heterodimers

| Combination | Fc chain | Mutation | Corresponding SEQ ID NO |
|---|---|---|---|
| 2 | A | Y349C + T366W + F405K | 9 |
|   | B | D356C + T366S + L368A + Y407V | 7 |
| 3 | A | Y349C + T366W + K409E | 10 |
|   | B | D356C + T366S + L368A + Y407V + F405K | 8 |
| 4 | A | Y349C + T366W + K409A | 11 |
|   | B | D356C + T366S + L368A + Y407V + F405K | 8 |

Example 2: Preparation and Investigation of ScFv-Fc/Fc Heterodimer

1. Constructing a Recombinant Vector Expressing a Mutated Fc Region of Human IgG1 and a ScFv-Fc Fusion Protein Based on an amino acid sequence (P01857) of a human immunoglobulin gamma1 (IgG1) constant region in a protein database (Uniprot), an amino acid sequence (SEQ ID NO:1) of a human IgG1-Fc region was obtained. By reverse transcription PCR, a nucleic acid fragment (SEQ ID NO:2), named as Fc gene) which encodes human IgG1-Fc was obtained from total RNA of human PBMC. By overlapping PCR, adding a coding sequence (as shown in SEQ ID NO: 3) of a kappaIII signal peptide of mouse at the 5'-terminal, and then subcloning it into a vector pcDNA4 (Invitrogen, Cat V86220), a recombinant expression vector for expression of a human IgG1-Fc (Fc for short) protein in mammalian cells was obtained.

A ScFv-Fc fusion protein coding gene (ScFv therein refers to an anti-HER2 single chain antibody) as shown in SEQ ID NO: 5 was obtained by artificial synthesis. The gene encoding a ScFv-Fc fusion protein sequence is shown in SEQ ID: 4, and was then subcloned to a mammalian cell expression vector pcDNA4 (Invitrogen, cat V86220) to obtain a recombinant expression vector for expressing the ScFv-Fc fusion protein in mammalian cells.

According to Table 2 of Example 1, a mutation combination of ScFv-Fc and Fc coding genes was performed by overlapping PCR, where the mutation of the chain A was located on the ScFv-Fc fusion protein, and the mutation of the chain B was located on the Fc protein. The mutant gene was subcloned to pcDNA4 (Invitrogen, cat V86220) to finally obtain the ScFv-Fc fusion protein to express mutations in mammalian cells and a recombinant expression vector of mutant Fc protein, respectively.

2. Transient Expression of a ScFv-Fc/Fc Heterodimer and Detection of the Influence of Different Mutation Combinations on Heterodimer Content Corresponding expression vectors of 4 mutation combinations in step 1, KH combination (as a reference group) and a wild-type combination (i.e., unmutated ScFv-Fc fusion protein and Fc protein as negative control group) were transfected into 293H suspension-culture cell (ATCC CRL-1573). Each mutation combination included cotransfection of recombinant expression vectors of the corresponding chain A (referring to ScFv-Fc fusion protein chain) and the chain B (referring to Fc protein chain), and the cotransfection ratio of recombinant expression vectors of the chain A to that of chain B was 1:1. After cultivation for 5-6 days, the transiently expressed culture supernatant was collected, and preliminarily purified transient transfection products of 4 groups of mutation combinations, KH mutation combination and wild-type negative control group were obtained by ProteinA affinity chromatography. Each of these transient transfection products contained different proportions of homodimer proteins (ScFv-Fc/ScFv-Fc, Fc/Fc) and heterodimer protein (ScFv-Fc/Fc). As the three proteins (ScFv-Fc/ScFv-Fc, Fc/Fc, and ScFv-Fc/Fc) had different molecular weights, the compositions of the homodimer protein (ScFv-Fc/ScFv-Fc, Fc/Fc) and the heterodimer protein (ScFv-Fc/Fc) in the product of each group could be detected by SDS-PAGE electrophoresis under non-reducing conditions, and the proportion of the homodimer protein (ScFv-Fc/ScFv-Fc, Fc/Fc) to the heterodimer protein (ScFv-Fc/Fc) was analyzed with Imagelab professional image analysis software provided by BioRad company. The electrophoresis test results are shown in FIG. 1 and Table 3.

TABLE 3

Ratio of Homodimer to Heterodimer in Transient Transfection Product for Various Mutation Combinations

| Mutation combination | Mutant amino acids on chain A (ScFv-Fc protein) | Mutant amino acids on chain B (Fc protein) | ScFv-Fc homodimer (%) | ScFv-FC/Fc heterodimer (%) | Proportion of Fc homodimer (%) |
|---|---|---|---|---|---|
| Wild-type control group | N.A. | N.A. | 59 | 35 | 6 |
| 1 | Y349C + T366W | D356C + T366S + L368A + Y407V + F405K | 24 | 58 | 18 |
| 2 | Y349C + T366W + F405K | D356C + T366S + L368A + Y407V | 10 | 70 | 20 |
| 3 | Y349C + T366W + K409E | D356C + T366S + L368A + Y407V + F405K | 25 | 57 | 18 |
| 4 | Y349C + T366W + K409A | D356C + T366S + L368A + Y407V + F405K | 10 | 77 | 13 |
| KH | Y349C + T366W | D356C + T366S + L368A + Y407V | 29 | 51 | 20 |

Compared with the wild-type negative control combination, the proportions of heterodimer (ScFv-Fc/Fc) in 4 groups of candidate mutation combinations and the KH combination were increased significantly. At the same time, on the basis of KH, after introducing new mutations, the proportion of heterodimers had also changed with the proportion of some heterodimers significantly increased (e.g., combinations 2,4) and the proportion of other heterodimers modestly improved (e.g., combinations 1,3). Here, it should be noted that new mutation combinations of the groups comprised regulation of two major interactions (spatial effect and ionic action) on interfacial side chain groups, and therefore, their impact on heterodimer contents cannot be simply considered as superposition of the two interactions. For example, combination 1 and combination 2 both introduced the F405K mutation to increase the repulsive force between homodimers, but combination 2 showed better effect than combination 1 in enhancing the heterodimer content (heterodimer content in the mutation combination 2 is about 70%, while combination 1 is about 58%). In addition, for the mutation introduced into K409, the heterodimer content was increased (77%) resulted from non-charged mutation in the mutation combination 4, which was more significant than that resulted from oppositely charged mutation in the mutation combination 3 (57%). However, similar effects should be resulted from the two mutation combination 1 and 4 if simply considering the superposition of the two interactions in theory.

In order to further investigate the influence of the cotransfection ratio of recombinant expression vectors of the chain A to those of the chain B on the ratio of homodimers to heterodimers, the cotransfection expression vectors used in two superior mutation combinations (2 and 4) and the KH combination were transfected with PEI to 293H suspension-culture cells (ATCC CRL-1573) at a ratio of 4:1 and 1:4, respectively, and the cell culture supernatant was collected after 5-6 days of cultivation. The respective transient transfection products were obtained through Protein A affinity chromatography. The compositions of homodimer proteins (ScFv-Fc/ScFv-Fc, Fc/Fc) and heterodimer proteins (ScFv-Fc/Fc) were detected by SDS-PAGE electrophoresis under non-reducing conditions. The specific results are shown in Table 4. As can be seen from the results, the cotransfection ratio of recombinant expression vectors had a significant influence on the ratio of homodimers and heterodimers in the product. The content of heterodimers in the product is significantly reduced at a cotransfection ratio of 4:1 and 1:4. The result shows that when expressions of the chain A and the chain B were relatively balanced, the three combinations could greatly enhance the proportion of heterodimers in the product and reduced the proportion of homodimers, but when expressions of the chain A and the chain B in the product are imbalanced, resultant excessive chain A or chain B would enhance the proportion of homodimers while reduced the heterodimer. In the KH combination, no matter which chain was excessive, the heterodimer content would be significantly reduced. Excessive chain B (Fc) in the mutation combination 2 had greater effect; while excessive chain A (ScFv-Fc) in the mutation combination 4 had greater effect. However, even if the chain B or chain A in the mutation combination 2 or the mutation combination 4 was excessive, the proportion of heterodimers formed thereof was still significantly higher than those in the KH combination of the control group. As can be seen through further analysis on the results, among the three mutation combinations, while the interaction between the chain A and the chain B has been significantly enhanced, the weakening degree of the interaction between the chain A and the chain A or between the chain B and the chain B was still insufficient, which further resulted in a fact that when one component thereof was excessively expressed, the balance between homodimers and heterodimers was broken, and more homodimers were produced. The new mutation combinations 2 and 4 therein had obvious optimization in preventing the formation of homodimers, compared to the KH combination.

TABLE 4

Influence of Different Cotransfection Ratios on the Ratio of Homodimers to Heterodimers

| Combination | Cotransfection ratio of recombinant expression vector of chain A (ScFv-Fc) to that of chain B (Fc) | ScFv-Fc in homodimer (%) | ScFv-Fc/Fc heterodimer (%) | Fc-Fc homodimer (%) |
|---|---|---|---|---|
| 2 | 4:1 | 23 | 66 | 11 |
|   | 1:4 | <1 | 49 | 51 |
| 4 | 4:1 | 46 | 53 | 1 |
|   | 1:4 | 4 | 66 | 30 |
| KH | 4:1 | 52 | 42 | 6 |
|   | 1:4 | 10 | 44 | 46 |

Example 3: Acquisition of Second Round Candidate Mutation Combination

On the basis of the preferred Fc mutation combinations (mutation combination 2 and mutation combination 4) mentioned in Examples 1 and 2, interfacial amino acid mutation was further introduced according to the disclosed three-dimensional crystal structure of wild-type Fc, so as to further reduce the mutual attraction between the chain A and the chain A and between the chain B and the chain B, and inhibit the formation of homodimer proteins.

According to the results in Table 1, an amino acid paired with a charged amino acid was further selected from contacting amino acids near mutation sites in the mutation combination 2 or mutation combination 4, and one amino acid on one chain therein (a non-charged amino acid was mutated to a charged amino acid, or a charged amino acid was mutated to a non-charged amino acid, or a charged amino acid was mutated to oppositely charged) was mutated in order to further improve the unbalance property of the ionic action between the chain A and the chain B, as well as to decrease the probability of homodimers formation or to increase the probability of formation of heterodimers at the same time.

For example, the contacting amino acid pair of Lys360 on chain A and Gln347 on chain B was mutated to change the ionic action therebetween. The two amino acid residues on one chain (e.g., chain A) thereof were mutated to negatively charged amino acid residues by, e.g., introducing mutations K360E and Q347E; non-charged amino acid residues on the other chain (e.g., chain B) were mutated to positively charged amino acid residues by, e.g., introducing mutation Q347R. Under the condition, when the chain A interacts with the chain A, the negative charge carried at 360th and 347th site would be mutually repulsive; when the chain B interacts with the chain B, the positive charge on the two sites would be mutually repulsive; and only when the chain A interacts with the chain B, the respective positive and negative charges thereof would attract each other. It was expected that such mutation would increase the mutual repulsion between the chain A and the chain A and between the chain B and the chain B, whilst increasing the mutual attraction between the chain A and the chain B.

Moreover, the amino acid residue of Leu368 was also investigated. The residue was surrounded by two charged amino acid residues: Glu357 and Lys409. Considering that the K409A mutation was introduced into the foregoing mutation combination 4, Leu368 on the Fc chain into which the K409A mutation was introduced (according to Example 2, here referred as the chain A) was further mutated to a negatively charged amino acid residue (e.g., 368E). Under the condition, when the chain A paired with the chain A, the negative charge carried by L368E on the two chains would interact with the negative charge carried by E357 to introduce a repulsive force; when chain A paired with chain B, the negative charge carried by L368E on chain A would not only repel the negative charge carried by E357 on chain B, but also attracted K409 on the chain B. Comprehensively, not too much repulsive force or attractive force was introduced. It was expected that such mutation would increase the mutual repulsion between the chain A and the chain A, but would not affect the interaction between the chain A and the chain B or between the chain B and the chain B.

Based on the preferred Fc mutation combinations (mutation combination 2 and mutation combination 4) mentioned in Examples 1 and 2, as well as the newly introduced mutation combination, the resulting mutation combinations are shown in Table 5:

Example 4: Preparation and Investigation of a New Round of ScFv-Fc/Fc Heterodimer Mutation Combination 1. Constructing a Recombinant Vector Expressing a Mutated Fc Region of Human IgG1 and a ScFv-Fc Fusion Protein According to Table 5 of Example 3, a recombined mutation of ScFv-Fc and Fc encoding genes was performed by overlapping PCR with the recombinant expression vector of the wild-type ScFv-Fc and Fc proteins constructed in Example 2 as the template, where the mutation of the chain A was located on the ScFv-Fc fusion protein, and the mutation of the chain B was located on the FC protein. The mutant gene was subcloned to pcDNA4 (Invitrogen, cat V86220) to finally obtain the ScFv-Fc fusion protein to express a new round of mutations in mammalian cells and a recombinant expression vector of the mutant Fc protein.

Figure 2:
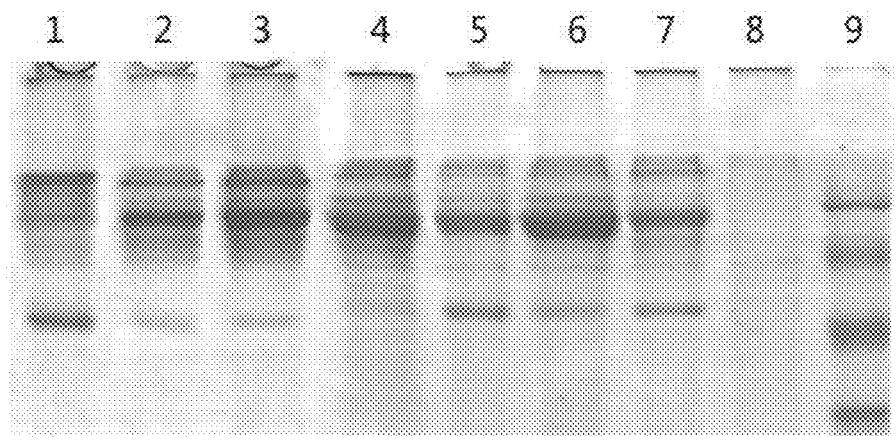
FIG. 2 shows the electrophoretic analysis result of transiently expressed ScFv-Fc/Fc heterodimer. 12% SDS-PAGE protein gel electrophoresis was used. Lanes 1 to 9 are successively: mutation combination 9, mutation combination 8, mutation combination 7, mutation combination 4, mutation combination 6, mutation combination 5, mutation combination 2, blank control (cell supernatant) and protein molecular mass markers. The homodimer and the heterodimer of products in each combination exhibit different migration distances in the gel electrophoresis due to molecular weight differences. Similar to FIG. 1, ScFv-Fc/ScFv-Fc homodimer, ScFv-Fc/Fc heterodimer and Fc/Fc homodimer are shown from top to bottom in FIG. 2.

2. Transient Expression of a ScFv-Fc/Fc Heterodimer and Detection of the Influence of Different Mutation Combinations on Heterodimer Content According to the method in Example 2-2, the 5 new mutation combinations (5 to 9) and the first round of preferred mutation combinations (2 and 4) was transiently expressed using 293H cells (ATCC CRL-1573). The cotransfection ratio of recombinant expression vector of the chain A to that of the chain B was 1:1. After 5-6 days of cultivation, the transiently expressed culture supernatant was collected, and 5 groups of preliminarily purified new mutation combinations and 2 groups of the first round of preferred combinations of transient transfection products were obtained by Protein A affinity chromatography. Each of these transient transfection products contained different proportions of homodimer proteins (ScFv-Fc/ScFv-Fc, Fc/Fc) and heterodimer protein (ScFv-Fc/Fc). As the three proteins (ScFv-Fc/ScFv-Fc, Fc/Fc, and ScFv-Fc/Fc) have different molecular weights, the compositions of the homodimer protein (ScFv-Fc/ScFv-Fc, Fc/Fc) and the heterodimer protein (ScFv-Fc/Fc) in the product of each group can be detected by SDS-PAGE electrophoresis under non-reducing conditions, and the proportion of the homodimer protein (ScFv-Fc/ScFv-Fc, Fc/Fc) to the heterodimer protein (ScFv-Fc/Fc) was analyzed with ImageLab professional image analysis software provided by Biorad company. The electrophoresis test results are shown in FIG. 2 and Table 6.

TABLE 5

List of Mutation Combinations of Heterodimers-2

| Combination | Fc chain | Mutation | Corresponding SEQ ID NO |
|---|---|---|---|
| 5 | A | Y349C + T366W + F405K + K360E + Q347E | 12 |
|   | B | D356C + T366S + L368A + Y407V + Q347R | 13 |
| 6 | A | Y349C + T366W + F405K + Q347R | 14 |
|   | B | D356C + T366S + L368A + Y407V + K360E + Q347E | 15 |
| 7 | A | Y349C + T366W + K409A + K360E + Q347E | 16 |
|   | B | D356C + T366S + L368A + Y407V + F405K + Q347R | 17 |
| 8 | A | Y349C + T366W + K409A + Q347R | 18 |
|   | B | D356C + T366S + L368A + Y407V + F405K + K360E + Q347E | 19 |
| 9 | A | Y349C + T366W + K409A + L368E | 20 |
|   | B | D356C + T366S + L368A + Y407V + F405K | 8 |

TABLE 6

Ratio of Homodimers and Heterodimers in Transient Transfection Product of Each Mutation Combination-2

| Mutation combination | Mutant amino acids on chain A (ScFv-Fc protein) | Mutant amino acids on chain B (Fc protein) | ScFv-Fc homodimer (%) | ScFv-FC/Fc heterodimer (%) | Proportion of Fc homodimer (%) |
|---|---|---|---|---|---|
| 2 | Y349C + T366W + F405K | D356C + T366S + L368A + Y407V | 17 | 60 | 23 |
| 5 | Y349C + T366W + F405K + K360E + Q347E | D356C + T366S + L368A + Y407V + Q347R | 14 | 72 | 14 |
| 6 | Y349C + T366W + F405K + Q347R | D356C + T366S + L368A + Y407V + K360E + Q347E | 14 | 62 | 24 |
| 4 | Y349C + T366W + K409A | D356C + T366S + L368A + Y407V + F405K | 21 | 69 | 10 |
| 7 | Y349C + T366W + K409A + K360E + Q347E | D356C + T366S + L368A + Y407V + F405K + Q347R | 24 | 64 | 12 |
| 8 | Y349C + T366W + K409A + Q347R | D356C + T366S + L368A + Y407V + F405K + K360E + Q347E | 21 | 71 | 8 |
| 9 | Y349C + T366W + K409A + L368E | D356C + T366S + L368A + Y407V + F405K | 39 | 30 | 31 |

Compared with the first round of the preferred mutation combinations, some newly introduced mutations had slightly increased the proportion of formation of heterodimers, such as the combination 5 over the combination 2; but a few groups had small changes, such as the combination 6 over the combination 2, and the combinations 7 and 8 over the combination 4. In addition, after new mutations were introduced into the combination 9, it contrarily greatly reduced the proportion of formation of heterodimers, presumably because the mutual repulsion between the negative charge carried by L368E newly introduced into the chain A and the negative charge carried by E357 on the chain B was more than the mutual attraction between the negative charge carried by L368E on the chain A and K409 on the chain B, resulting in an unstable heterodimer. In general, some groups of the newly introduced mutations appropriately contributed to the formation of heterodimers, but did not bring significant improvements.

In order to further investigate the influence of the newly introduced mutations on AA homodimer and BB homodimers, proteins of the chain A or proteins of the chain B were separately transiently expressed, and the tendency of forming homodimers was investigated by comparing the homodimer protein expression level under equivalent transient transfection conditions. The recombinant expression vector was transfected with PEI into suspension-cultured 293H cells (ATCC CRL-1573), and the cell supernatant was collected after 5-6 days of cultivation. The respective transient transfection product was obtained through Protein A affinity chromatography, and the expression levels thereof were detected by OD280. The results are shown in Table 7. As can be seen from the expression level, some mutations (combination 8, combination 9) introduced into the chain A of the combination 4 could reduce the tendency of forming homodimers thereof; some mutations (combination 5) introduced into the chain B of the combination 2 could reduce the tendency of forming homodimers; and the remaining new mutations had little effect on the formation of homodimers. Moreover, as can be further seen from the results, the combination 2 and its derivative combinations (5, 6) exhibited a smaller tendency of forming the homodimers of the chain A compared with the mutation combination 4 and its derivative combinations (7, 8, 9); and the latter exhibited a smaller tendency of forming the homodimers of chain B compared with the former. The results were consistent with the results obtained in Example 2, and further proved the feasibility of preliminary investigation of the tendency of forming homodimer using the method. In addition, the expression levels of all the B chains were far lower than those of the chain A. It was found through separate transient expression of the wild-type chain A and the wild-type chain B that, when not any mutation was introduced, the expression level of homodimers of the wild-type chain B was lower than that of the wild-type chain A (the former was about half of the latter). Therefore, it was inferred that the N-terminal of the Fc sequence in the chain A was fused with the ScFv sequence, which helped to enhance its expression level. However, the difference between the expression level of the chain A and that of the chain B cannot directly reflect the difference of tendency between forming AA homodimers and forming BB homodimers.

TABLE 7

Comparison of the Expression Levels of Homodimers in Case of Separate Transient Transfection of Chain A or Chain B in Each Mutation Combination

| Mutation combination | Mutant amino acids on chain A (ScFv-Fc protein) | Expression levels of AA homodimers in case of separate expression | Mutant amino acids on chain B (Fc protein) | Expression levels of BB homodimers in case of separate expression |
|---|---|---|---|---|
| 2 | Y349C + T366W + F405K | 48 mg/L | D356C + T366S + L368A + Y407V | 55 mg/L |
| 5 | Y349C + T366W + F405K + K360E + Q347E | 46 mg/L | D356C + T366S + L368A + Y407V + Q347R | 36 mg/L |
| 6 | Y349C + T366W + F405K + Q347R | 40 mg/L | D356C + T366S + L368A + Y407V + K360E + Q347E | 58 mg/L |
| 4 | Y349C + T366W + K409A | 111 mg/L | D356C + T366S + L368A + Y407V + F405K | 21 mg/L |
| 7 | Y349C + T366W + K409A + K360E + Q347E | 110 mg/L | D356C + T366S + L368A + Y407V + F405K + Q347R | 18 mg/L |
| 8 | Y349C + T366W + K409A + Q347R | 96 mg/L | D356C + T366S + L368A + Y407V + F405K + K360E + Q347E | 21 mg/L |
| 9 | Y349C + T366W + K409A + L368E | 10 mg/L | D356C + T366S + L368A + Y407V + F405K | 20 mg/L |

Example 5: Acquisition of Third Round Candidate Mutation Combination

1. According to the Crystal Structure of the Mutation Combination 4, in Conjunction with Structural Modeling, Candidate Amino Acid Mutation Sequence on a New Contact Interface was Found Out to Further Inhibit the Formation of Homodimer Proteins or Promote the Formation of Heterodimer Proteins on the Basis of the Original Mutation Combinations (e.g., Mutation Combination 2 or 4).

Crystallographic Structure Analysis on Heterodimer Proteins of the Mutation Combination 4

Mutation combination 4 was selected to obtain a heterodimer protein of mutation combination 4 by transient expression in 293H cells (ATCC CRL-1573) and purification, and the crystal structure was analyzed. Here, a fragment of His-tag sequence was inserted into the C-terminal of the chain B of the mutation combination 4 using molecular cloning, so as to obtain a pure AB heterodimer protein using the IMAC method for crystallization after Protein A affinity chromatography.

Crystallographic structure was analyzed as follows:
The heterodimer Fc crystal was formed under the following conditions: mixing 2 μL, of a crystallization buffer (15% PEG3350, 1 M LiCl and 0.1 M MES at pH6.0) with 2 μL of a protein solution (10 mg/mL target protein, 10 mM Tris and 150 mM NaCl at pH 7.4), and was left to stand for crystallization at 22° C. The crystal grew about 3 days later. The crystal was then placed in the following solution: 17% PEG3350, 1M LiCl, 0.1M MES and 20% glycerin at pH6.0; and then quickly infiltrated and frozen in liquid nitrogen. The X-diffraction data was collected by SSRF BL17U. The structure of the wild-type Fc (PDB landing number: 3AVE) was used as the framework to analyze the molecular replacement structure.

Figure 3:
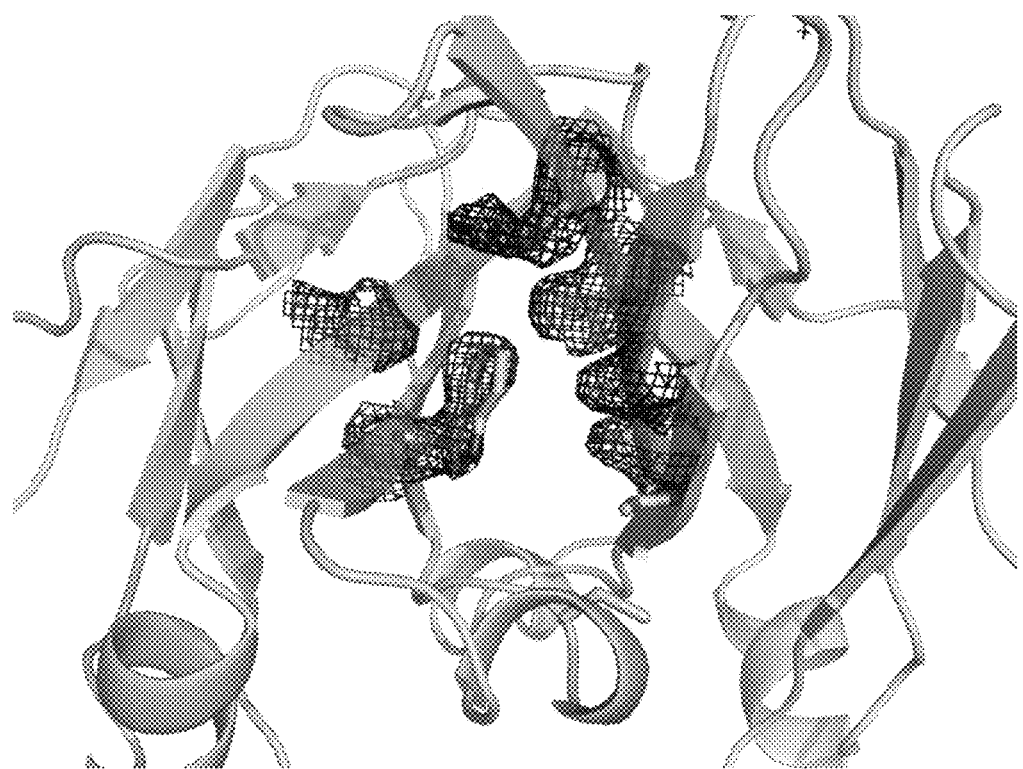
FIG. 3 shows a partial view of a crystal structure of CH3-CH3 interface of a heterodimer Fc in the mutation combination 4. Mutated amino acid residues are shown by short sticks, and specifically contain the following mutually contacting mutated amino acid residue pairs: T366W/A chain-T366S, L368A, Y407V/B chain, K409A/A chain-F405K/B chain and S354C/A chain-Y349C/B chain. Chain A (the left chain in a slightly lighter color) is indicated in green, and chain B (the right chain in a slightly darker color) is indicated in light blue.

The crystal structure showed that the overall structure of the mutant Fc heterodimer was similar to that of the wild-type Fc, but was changed on some degree on the CH3 interface into which mutations were introduced due to the interaction between different side chain groups. The specific crystal structure of the CH3 interface is shown in FIG. 3.

2. Acquisition of New Candidate Mutation Combinations

A new candidate mutation was further screened according to the result of the crystal structure of the mutation combination 4.

First of all, it was found through the three-dimensional crystal structure that Y349C on chain A and D356C on chain B could not form a disulfide bond because of the directions of two side chain groups of Cys, but formed a pair of free sulfhydryls. According to this result, this pair of mutations would not be performed in the third round of mutation, and restored to the wild-type amino acid sequence before the mutation.

Figure 4:
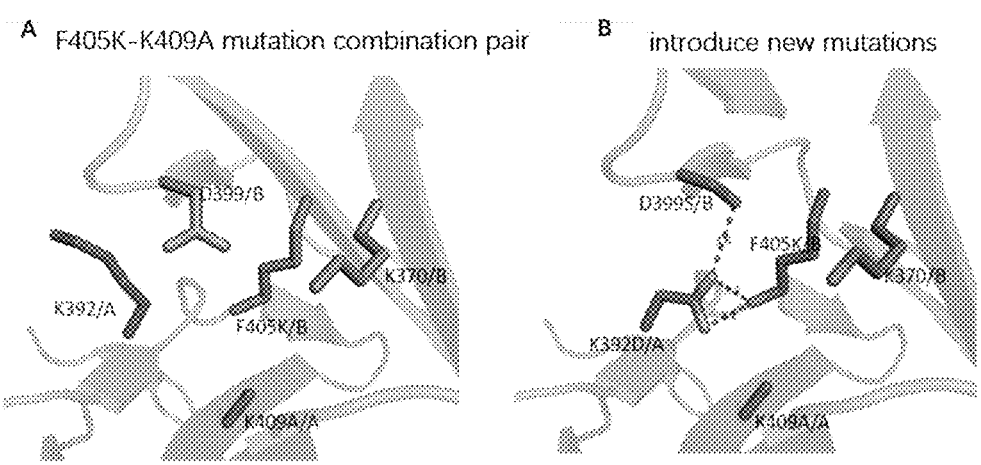
FIG. 4 shows that introducing a new pair of mutations D399S-K392D at a site near the amino acid residue pair of mutations F405K-K409A can further enhance the mutual attraction between heterodimers as well as mutual repulsion between homodimers.

Secondly, by comparing the three-dimensional structural modeling, mutations were further introduced near a pair of mutated amino acid residues F405K-K409A to change the ionic bonding and hydrogen bonding. If K409A was on chain A, and F405K was on chain B, then K392D mutation would be introduced into the chain A, and D399S mutation would be introduced into the chain B. As shown in FIG. 4, for the interaction between the chain A and the chain B, the ionic bond between K392D and F405K and the hydrogen bond between K392D and D399S were added to the newly introduced mutation pair, which was expected to improve the tendency of forming heterodimers. The electrostatic repulsion between K329D and D399 was introduced into the interaction between the chain A and the chain A to inhibit the formation of AA homodimers. In the interaction between the chain B and the chain B, the ionic bond between the original K409 and D399 disappeared due to the introduction of the D399S mutation, thereby reducing the trend of forming BB homodimers.

Thirdly, comparison of the crystal structure of the mutation combination 4 with the wild-type Fc protein crystal structure showed that, the chain A of the mutation combination 4 had outward shift (away from the chain B), presumably because largened side chain groups in the T366W mutation of the chain A brought certain spatial steric hindrance. On this basis, amino acid residues of the chain B which contacted with the T366W residue on the chain A were further mutated to amino acid residues with smaller side chain groups. For example, the original Y407V and L368A mutations on the chain B were replaced with Y407A and L386G mutations to leave enough space for the T366W mutation, which may further stabilize the heterodimer structure.

Fourthly, in the peripheral of the mutant amino acid residue pair F405K-K409A, other amino acids on the contact interface were mutated to change the interfacial electrostatic interaction. Here, the contacting amino acid pair Y349 and E357 was investigated. The mutation Y349D was introduced into the chain A, and E357A was introduced into the chain B. The electrostatic repulsion introduced between Y349D and E357A of the chain A and the chain A would hinder the formation of AA homodimers. No new interaction was introduced between the chain A and the chain B and between the chain B and the chain B. On this basis, S354D mutation was further introduced into the chain A to strengthen the electrostatic repulsion thereof with E357A so as to further hinder the formation of AA homodimers.

A mutation combination as shown in Table 8 was obtained by introducing the above mutation on the basis of the mutation combination 4:

TABLE 8

List of Mutation Combinations of Heterodimers-3

| Combination | Fc chain | Mutation | Corresponding SEQ ID NO |
|---|---|---|---|
| 10 | A | T366W + K409A + K392D | 21 |
| | B | T366S + L368A + Y407V + D399S + F405K | 22 |
| 11 | A | T366W + K409A | 23 |
| | B | T366S + L368G + Y407A + F405K | 24 |
| 12 | A | T366W + K409A + Y349D | 21 |
| | B | T366S + L368A + Y407V + F405K + E357A | 25 |
| 13 | A | T366W + K409A + Y349D + S354D | 26 |
| | B | T366S + L368A + Y407V + F405K + E357A | 25 |

Then, a mutation combination as shown in Table 9 was obtained by introducing the above mutation on the basis of the mutation combination 2 whilst referring to the mutation combination 4.

TABLE 9

List of Mutation Combinations of Heterodimers-4

| Combination | Fc chain | Mutation | Corresponding SEQ ID NO |
|---|---|---|---|
| 14 | A | T366W + F405K | 27 |
| | B | T366S + L368A + Y407V + K409A | 28 |
| 15 | A | T366W + F405K + D399S | 29 |
| | B | T3665 + L368A + Y407V + K409A + K392D | 30 |
| 16 | A | T366W + F405K | 27 |
| | B | T366S + L368G + Y407A + K409A | 31 |
| 17 | A | T366W + F405K + Y349D | 32 |
| | B | T366S + L368A + Y407V + K409A + E357A | 33 |
| 18 | A | T366W + F405K + Y349D + S354D | 34 |
| | B | T366S + L368A + Y407V + K409A + E357A | 33 |

Example 6: Preparation and Investigation of a Third Round of ScFv-Fc/VhH-Fc Heterodimer Mutation Combination 1. Constructing a Recombinant Vector Expressing a Mutated Fc Region of Human IgG1 and a ScFv-Fc Fusion Protein Considering that the expression level of pure Fc regions was lower than that of ScFv-Fc, in order to better grasp the expression ratio of the two chains, a variable region sequence (labeled as VhH) of a single domain antibody of a camel was fused at the N terminal of the original B chain (simple Fc chain). A gene encoding VhH-Fc fusion protein is shown in SEQ ID NO: 36 obtained by artificial synthesis. This gene encodes a VhH-Fc fusion protein which has a sequence shown in SEQ ID:35, and the gene was then subcloned to a mammalian cell expression vector pcDNA4 (Invitrogen, cat V86220) to obtain a recombinant expression vector for expressing the VhH-Fc fusion protein in mammalian cells.

According to Table 8 of Example 5, a combined mutation of ScFv-Fc and VhH-Fc encoding genes (SEQ ID NO:5 and SEQ ID NO:36) was performed by overlapping PCR with the recombinant expression vector of the wild-type ScFv-Fc protein constructed in Example 2 and the recombinant expression vector of the VhH-Fc fusion protein as the templates, where the mutation of the chain A was located on the ScFv-Fc fusion protein, and the mutation of the chain B was located on the VhH-Fc protein. The mutant gene was subcloned to pcDNA4 (Invitrogen, cat V86220) to finally obtain the ScFv-Fc fusion protein to express a third round of mutations in mammalian cells and a recombinant expression vector of the mutant VhH-Fc protein (SEQ ID NO:4 to SEQ ID NO:35).

2. Transient Expression of a ScFv-Fc/VhH-Fc Heterodimer and Detection of the Influence of Different Mutation Combinations on Heterodimer Content According to the method in Example 2-2, the 4 mutation combinations (10 to 13) in Table 8 and the mutation combination 4 were transiently expressed using 293H cells (ATCC CRL-1573). The cotransfection ratio of recombinant expression vector of the chain A to that of the chain B was 4:1, 1:1 and 1:4. After 5-6 days of cultivation, the transiently expressed culture supernatant was collected, and 4 groups of preliminarily purified new mutation of combinations and transient transfection products of the mutation combination 4 were obtained by Protein A affinity chromatography. Each of these transient transfection products contained different proportions of homodimer proteins (ScFv-Fc/ScFv-Fc, VhH-Fc/VhH-Fc) and heterodimer protein (ScFv-Fc/VhH-Fc). As the three proteins (ScFv-Fc/ScFv-Fc, VhH-Fc/VhH-Fc and ScFv-Fc/VhH-Fc) had different molecular weights, the compositions of the homodimer protein (ScFv-Fc/ScFv-Fc, VhH-Fc/VhH-Fc) and the heterodimer protein (ScFv-Fc/VhH-Fc) in the product of each group could be detected by SDS-PAGE electrophoresis under non-reducing conditions, and the proportions of the homodimer protein (ScFv-Fc/ScFv-Fc, VhH-Fc/VhH-Fc) and the heterodimer protein (ScFv-Fc/VhH-Fc) were analyzed with ImageLab professional image analysis software provided by Biorad company at the same time. The electrophoresis test results were shown in Table 10.

TABLE 10

Ratio of Homodimers to Heterodimers in Transient Transfection Products of Each Mutation Combination-3

| Combination | Cotransfection ratio of vector of chain A (ScFv-Fc) to that of chain B (VhH-Fc) in | ScFv-Fc homodimer (%) | ScFv-Fc/VhH-Fc heterodimer (%) | VhH-Fc homodimer (%) |
|---|---|---|---|---|
| 4 | 4:1 | 46 | 54 | <1 |
|   | 1:1 | 13 | 68 | 19 |
|   | 1:4 | <1 | 47 | 53 |
| 10 | 4:1 | 39 | 61 | <1 |
|    | 1:1 | 7  | 80 | 13 |
|    | 1:4 | <1 | 73 | 27 |
| 11 | 4:1 | 52 | 52 | 0 |
|    | 1:1 | 15 | 85 | 0 |
|    | 1:4 | 11 | 89 | 0 |
| 12 | 4:1 | 48 | 49 | 3 |
|    | 1:1 | 14 | 83 | 3 |
|    | 1:4 | 9  | 60 | 31 |
| 13 | 4:1 | 37 | 61 | 2 |
|    | 1:1 | 10 | 84 | 6 |
|    | 1:4 | 2  | 64 | 34 |

In order to further investigate the influence of the newly introduced mutations on AA homodimer and BB homodimers, proteins of the chain A or proteins of the chain B were separately transiently expressed, and the tendency of forming homodimers was investigated by comparing the expression levels of homodimer protein under equivalent transient transfection conditions. The recombinant expression vector was transfected with PEI into suspension-cultured 293H cells (ATCC CRL-1573), and the cell supernatant was collected after 5-6 days of cultivation. The respective transient transfection products were obtained through Protein A affinity chromatography, and the expression levels thereof were detected by OD280. The results were shown in Table 11.

that in the mutation combination 4. In the mutation combination 11, new mutations for the chain B could almost completely hinder the formation of BB homodimers. It can be seen that even at the transient transfection ratio of 1:4 (A:B), the BB homodimer was still not observed, and the heterodimer content reached 89%.

According to the results of the combinations 10 to 13, mutation combination 15, 16 and 18 were further selected to investigate their influence on the formation of heterodimers by transient expression.

According to the method in Example 2-2, the 3 mutation combinations (15, 16 and 18) in Table 9 and the mutation combination 2 were transiently expressed using 293H cells (ATCC CRL-1573). The cotransfection ratio of recombinant

TABLE 11

Comparison of the Expression Levels of AA Homodimers and BB Homodimers in Each Mutation Combination-2

| Mutation combination | Mutant amino acids on chain A (ScFv-Fc protein) | Expression levels of AA homodimers in case of separate expression | Mutant amino acids on chain B (Fc protein) | Expression levels of BB homodimers in case of separate expression |
|---|---|---|---|---|
| 4  | Y349C + T366W + K409A | 365 mg/L | D356C + T366S + L368A + Y407V + F405K | 293 mg/L |
| 10 | T366W + K409A + K392D | 370 mg/L | T366S + L368A + Y407V + D399S + F405K | 76 mg/L |
| 11 | T366W + K409A | 342 mg/L | T366S + L368G + Y407A + F405K | <6 mg/L |
| 12 | T366W + K409A + Y349D | 354 mg/L | T366S + L368A + Y407V + F405K + E357A | 66 mg/L |
| 13 | T366W + K409A + Y349D + S354D | 308 mg/L | T366S + L368A + Y407V + F405K + E357A | 66 mg/L |

Through comprehensively considering the above results, it was found that after introducing the third round of mutation into the mutation combination 4, it did not show significant effect in inhibiting the formation of AA homodimers, but significantly hindered the formation of BB homodimers, and effectively promoted the formation of heterodimers. When the expressions of the two chains were close to equilibrium (1:1), each of the contents of heterodimers in groups of new mutation combinations reached more than 80%, and was significantly improved compared with expression vector of the chain A to that of the chain B was 4:1, 1:1 and 1:4. The transiently expressed culture supernatant was collected after 5-6 days of cultivation. And transient transfection products of 3 new preliminarily purified mutation combinations and the mutation combination 2 were obtained by Protein A affinity chromatography. Each of these transient transfection products contained different proportions of homodimer proteins (ScFv-Fc/ScFv-Fc, VhH-Fc/VhH-Fc) and heterodimer protein (ScFv-Fc/VhH-Fc). As the three proteins (ScFv-Fc/ScFv-Fc, VhH-Fc/VhH-Fc and ScFv-Fc/VhH-Fc) had different molecular weights, the compositions of the homodimer protein (ScFv-Fc/ScFv-Fc, VhH-Fc/VhH-Fc) and the heterodimer protein (ScFv-Fc/VhH-Fc) in the product of each group could be detected by SDS-PAGE electrophoresis under non-reducing conditions, and the proportion of the homodimer protein (ScFv-Fc/ScFv-Fc, VhH-Fc/VhH-Fc) and the heterodimer protein (ScFv-Fc/VhH-Fc) was analyzed with ImageLab professional image analysis software provided by Biorad company at the same time, and the electrophoresis test results were shown in Table 12. It can be seen that after introducing the third round of mutation into the mutation combination 2, it also showed significant effect in hindering the formation of BB homodimers, and enhanced the formation of heterodimers. When the expressions of the two chains were close to equilibrium (1:1), each of the contents of heterodimers in new combinations could reach more than 80% which was significantly enhanced compared with the mutation combination 4. When the proportion of the transient transfection vector was appropriately changed in the mutation combinations 16 and 18 (plasmid of chain B was excessive or plasmids of the two chains were balanced), the proportion of heterodimers thereof was still more than 80%.

TABLE 12

Ratio of Homodimers to Heterodimers in Transient Transfection Products of Each Mutation Combination-4

| Combination | Cotransfection ratio of vector of chain A (ScFv-Fc) to that of chain B (VhH-Fc) | ScFv-Fc homodimer (%) | ScFv-Fc/VhH-Fc heterodimer (%) | VhH-Fc homodimer (%) |
|---|---|---|---|---|
| 2 | 4:1 | 28 | 55 | 17 |
| | 1:1 | 9 | 64 | 27 |
| | 1:4 | <1 | 39 | 61 |
| 15 | 4:1 | 28 | 66 | 6 |
| | 1:1 | 6 | 81 | 13 |
| | 1:4 | <1 | 69 | 31 |
| 16 | 4:1 | 23 | 77 | <1 |
| | 1:1 | 5 | 88 | 7 |
| | 1:4 | 3 | 93 | 4 |
| 18 | 4:1 | 29 | 61 | 10 |
| | 1:1 | 9 | 84 | 7 |
| | 1:4 | 5 | 86 | 9 |

Example 7: Assessment on Other Features of Heterodimers

1. Accelerated Stability Test of Heterodimers

Heterodimers of the mutation combinations 4, 11 and 16 were selected for accelerated stability test with PBS as the buffer at a temperature of 45° C. with an experimental period of 31 days. The heterodimers were tested with non-reducing CE-SDS on 0th day, 8th day, 18th day and 31st day, which were compared with the corresponding wild-type Fc protein. The SDS-PAGE results of the 31-day accelerated stability test showed that each of the main peak contents of the three mutation samples and wild-type control samples decreased by no more than 2% until the 31st day. It can be concluded that the heterodimer exhibited same thermal stability as the wild-type one.

While the specific embodiments of the invention according to the present disclosure have been described in detail, and will be understood by those skilled in the art, but the details can be modified and substituted according to all disclosed inspirations, and all of these changes fall within the protection scope of the invention according to the present disclosure. It is intended that the appended claims and other equivalents thereof define the entire scope of the invention.

The invention claimed is:

1. A heterodimer molecule, comprising a first polypeptide chain and a second polypeptide chain, wherein said first polypeptide chain comprises a first CH3 domain of an antibody heavy chain constant region, said second polypeptide chain comprises a second CH3 domain of an antibody heavy chain constant region, wherein said first CH3 domain and said second CH3 domain differ from a corresponding wild-type CH3 domain of a human antibody heavy chain constant region by amino acid mutations, wherein the amino acid mutations consist of substitution mutations selected from one of groups (1) to (4):

(1) in said first CH3 domain: T366+K409+K392, in said second CH3 domain: T366+L368+Y407+D399+F405;
(2) in said first CH3 domain: T366+K409, in said second CH3 domain: T366+L368+Y407+F405;
(3) in said first CH3 domain: T366+K409+Y349, in said second CH3 domain: T366+L368+Y407+F405+E357; and
(4) in said first CH3 domain: T366+K409+Y349+S354, in said second CH3 domain: T366+L368+Y407+F405+E357;

wherein in said first CH3 domain:
said amino acid mutation at T366 is T366W;
said amino acid mutation at K409 is K409A;
said amino acid mutation at K392 is K392D;
said amino acid mutation at Y349 is Y349D; and
said amino acid mutation at S354 is S354D;
and wherein in said second CH3 domain:
said amino acid mutation at T366 is T366S;
said amino acid mutation at L368 is L368A and said amino acid mutation at Y407 is Y407V; or said amino acid mutation at L368 is L368G and said amino acid mutation at Y407 is Y407A;
said amino acid mutation at D399 is D399S;
said amino acid mutation at F405 is F405K; and
said amino acid mutation at E357 is E357A;
wherein said amino acid is numbered according to the EU index of the KABAT numbering of the antibody Fc region; and wherein said wild-type CH3 domain of the human antibody heavy chain constant region is a CH3 domain of a human IgG1 heavy chain constant region.

2. The heterodimer molecule according to claim 1, wherein said first CH3 domain and said second CH3 domain comprise one group of amino acid mutations selected from the following groups:

1) said first CH3 domain: T366W+K409A+K392D, said second CH3 domain: T366S+L368A+Y407V+D399S+F405K;
2) said first CH3 domain: T366W+K409A, said second CH3 domain: T366S+L368G+Y407A+F405K;
3) said first CH3 domain: T366W+K409A+Y349D, said second CH3 domain: T366S+L368A+Y407V+F405K+E357A;
4) said first CH3 domain: T366W+K409A+Y349D+S354D, said second CH3 domain: T366S+L368A+Y407V+F405K+E357A.

3. The heterodimer molecule according to claim 1, wherein said first polypeptide chain and said second polypeptide chain further comprise a CH2 domain of an antibody heavy chain constant region, respectively.

4. The heterodimer molecule according to claim 1, wherein said first polypeptide chain and said second polypeptide chain further comprise a hinge region of an antibody heavy chain constant region or a part thereof, respectively.

5. The heterodimer molecule according to claim 1, wherein said first polypeptide chain and/or said second polypeptide chain further comprise a molecule binding region, and said molecule binding region comprises an antigen binding region.

6. The heterodimer molecule according to claim 5, wherein said antigen binding region comprises an antibody variable region.

7. The heterodimer molecule according to claim 1, wherein said heterodimer molecule is a bispecific antibody, a bispecific fusion protein or an antibody-fusion protein chimera.

8. A composition, comprising the heterodimer molecule according to claim 1, and optionally a pharmaceutically acceptable carrier or excipient.

\* \* \* \* \*